United States Patent
Klein

(10) Patent No.: US 12,059,265 B1
(45) Date of Patent: Aug. 13, 2024

(54) MEDICAL ASSESSMENT DEVICE AND SYSTEM FOR DIAGNOSES OF NEUROLOGICAL AND OTHER CONDITIONS

(71) Applicant: Strok3, LLC, Green Cove Springs, FL (US)

(72) Inventor: Matthew Hayner Klein, Lafayette, CA (US)

(73) Assignee: STROK3, LLC, Green Cove Springs, FL (US)

( * ) Notice: Subject to any disclaimer, the term of this patent is extended or adjusted under 35 U.S.C. 154(b) by 0 days.

(21) Appl. No.: 18/397,916

(22) Filed: Dec. 27, 2023

(51) Int. Cl.
A61B 5/00 (2006.01)
A61B 5/11 (2006.01)
G16H 50/20 (2018.01)

(52) U.S. Cl.
CPC .......... *A61B 5/4088* (2013.01); *A61B 5/1124* (2013.01); *A61B 5/4803* (2013.01); *A61B 5/7475* (2013.01); *G16H 50/20* (2018.01)

(58) Field of Classification Search
CPC .... A61B 5/4088; A61B 5/4803; A61B 5/7475
See application file for complete search history.

(56) References Cited

U.S. PATENT DOCUMENTS

| | | | |
|---|---|---|---|
| 10,614,288 B2 | 4/2020 | Kusens et al. | |
| 10,846,518 B2 | 11/2020 | Chang et al. | |
| 10,952,613 B2 | 3/2021 | Kim et al. | |
| 11,241,169 B2 | 2/2022 | Kusens et al. | |
| 2017/0007167 A1 | 1/2017 | Kostic et al. | |
| 2022/0031162 A1 | 2/2022 | Greenwood et al. | |
| 2022/0101999 A1* | 3/2022 | Bonutti | A61N 1/3605 |
| 2023/0062081 A1* | 3/2023 | Kuperman | G16H 40/67 |

* cited by examiner

*Primary Examiner* — Tammie K Marlen
(74) *Attorney, Agent, or Firm* — Volpe Koenig

(57) ABSTRACT

A system for a neurological assessment is provided. The system includes a memory storing instructions for the neurological assessment. The system includes a display, an audio output, a camera, a microphone, and a processor operably coupled thereto. The processor executes the instructions to cause the system to prompt a patient to perform actions, record video and audio of the actions as non-standardized patient specific information via the camera and the microphone, and generate relevant clipped portions from the video and the audio. The relevant clipped portions convert the non-standardized patient specific information into standardized patient specific information. The processor executes the instructions to cause the system to cause a determination of a neurologic status for the patient based on the standardized patient specific information by transmitting the relevant clipped portions to a second system for analysis and receiving an analysis result including the neurologic status from the second system.

33 Claims, 7 Drawing Sheets

MEDICAL ASSESSMENT DEVICE AND SYSTEM FOR DIAGNOSES OF NEUROLOGICAL AND OTHER CONDITIONS

FIELD OF INVENTION

The present invention relates generally to a medical assessment device and system, and particularly to a method, a device, and a system for medical assessments for diagnosis of neurological and other conditions.

BACKGROUND

Stroke represents a leading cause of death and a most significant cause of disability in the world, with an annual mortality of 5.5 million. For example, ischemic stroke is a leading cause of death and disability in the United States. Stroke also represents significant healthcare costs in Europe with an annual cost of 60 billion EUR and in the USA with an annual cost of 45.5 billion USD. Common risk factors for a stroke include, but are not limited to, high blood pressure, smoking, and atrial fibrillation. The impact of stroke on society is also not confined to acute management, as rehabilitation, medical care of chronic management, social services, and informal caregiving have huge direct and indirect costs.

Several treatments have been proposed for stroke management. Yet, every fifteen (15) minutes of delay in an administration of reperfusion therapies (e.g., thrombolysis and thrombectomy) leads to an increased risk of long-term disability, in-hospital mortality, and intraparenchymal hemorrhage. Further, healthcare costs are also associated with the timing of reperfusion therapy, with delays being associated with a reduction in quality-adjusted life years and the economic value of care.

Conventionally technology, which may assist clinicians or providers with making diagnosis, has been limited in speeding up stroke management, following proper treatment protocols, and lacking in proper follow through when a patient is in fact a candidate for thrombolytics (e.g., clot busting drug) but does not receive it. Further, to the extent that conventional technology assist clinicians or providers, conventional technology lacks any abilities to provide immediate and comprehensive evaluations of stroke patients with complex and nuanced neurological exams and to provide training and experience to clinicians or providers to complete these evaluations (e.g., conventional technologies lack stroke identification and clinical evaluation).

Thus, a solution is needed for medical assessments for diagnoses of neurological and other conditions.

SUMMARY

According to one or more embodiments, a system for a neurological assessment is provided. The system includes a memory. The memory includes processor executable instructions for the neurological assessment. The system includes a display, an audio output, a camera, a microphone, and a processor operably coupled to the memory, the display, the audio output, the camera, and the microphone. The processor is configured to execute the processor executable instructions for the neurological assessment to cause the system to prompt a patient to perform at least one of a plurality of actions, record video and audio of the at least one of a plurality of actions as non-standardized patient specific information from the patient via the camera and the microphone, and generate one or more relevant clipped portions from the video and the audio. The one or more relevant clipped portions convert the non-standardized patient specific information into standardized patient specific information. The processor is configured to execute the processor executable instructions for the neurological assessment to cause the system to cause a determination of a neurologic status for the patient based on the standardized patient specific information by transmitting the one or more relevant clipped portions to a second system for analysis and receiving an analysis result comprising the neurologic status from the second system.

According to one or more embodiments, a system for a neurological assessment is provided. The system includes a memory. The memory includes processor executable instructions for the neurological assessment. The system includes a display, an audio output, a camera, a microphone, and a processor operably coupled to the memory, the display, the audio output, the camera, and the microphone. The processor is configured to execute the processor executable instructions for the neurological assessment to cause the system to prompt a patient to perform at least one of a plurality of actions and record video and audio of the at least one of a plurality of actions as non-standardized patient specific information from a patient via the camera and the microphone. The processor is configured to execute the processor executable instructions for the neurological assessment to cause the system to process one or more relevant clipped portions of the video and the audio to produce a neurological assessment score for the patient. The one or more relevant clipped portions summarize the non-standardized patient specific information into a standardized patient specific information. The processor is configured to execute the processor executable instructions for the neurological assessment to cause the system to determine a neurologic status for the patient based on the neurological assessment score and implement a neurological response based on the neurologic status.

According to one or more embodiments, a method for a neurological assessment of a patient is provided. The method is implemented by a system including at least a memory, a display, an audio output, a camera, a microphone, and a processor. The method includes prompting the patient to perform at least one of a plurality of actions, recording video and audio of the at least one of a plurality of actions as non-standardized patient specific information from the patient via the camera and the microphone, and generating one or more relevant clipped portions from the video and the audio. The one or more relevant clipped portions convert the non-standardized patient specific information into standardized patient specific information. The method includes causing a determination of a neurologic status for the patient based on the standardized patient specific information by transmitting the one or more relevant clipped portions to a second system for analysis and receiving an analysis result comprising the neurologic status from the second system.

According to one or more embodiments, a method for a neurological assessment of a patient is provided. The method is implemented by a system including at least a memory, a display, an audio output, a camera, a microphone, and a processor. The method includes prompting a patient to perform at least one of a plurality of actions and record video and audio of the at least one of a plurality of actions as non-standardized patient specific information from a patient via the camera and the microphone. The method includes scoring one or more relevant clipped portions of the video and the audio to produce a neurological assessment score for the patient. The one or more relevant clipped portions summarize the non-standardized patient specific information into a standardized patient specific information. The method includes determining a neurologic status for the patient based on the neurological assessment score; and implementing a neurological response based on the neurologic status.

According to one or more embodiments, any of the methods and systems herein can be implemented as a method, a system, an apparatus, a device, and/or an environment.

These and other features of the present invention will become readily apparent upon further review of the following specification and drawings.

BRIEF DESCRIPTION OF THE DRAWINGS

A more detailed understanding may be had from the following description, given by way of example in conjunction with the accompanying drawings, wherein like reference numerals in the figures indicate like elements, and wherein.

Similar reference characters denote corresponding features consistently throughout the attached drawings.

DETAILED DESCRIPTION

Figure 1:
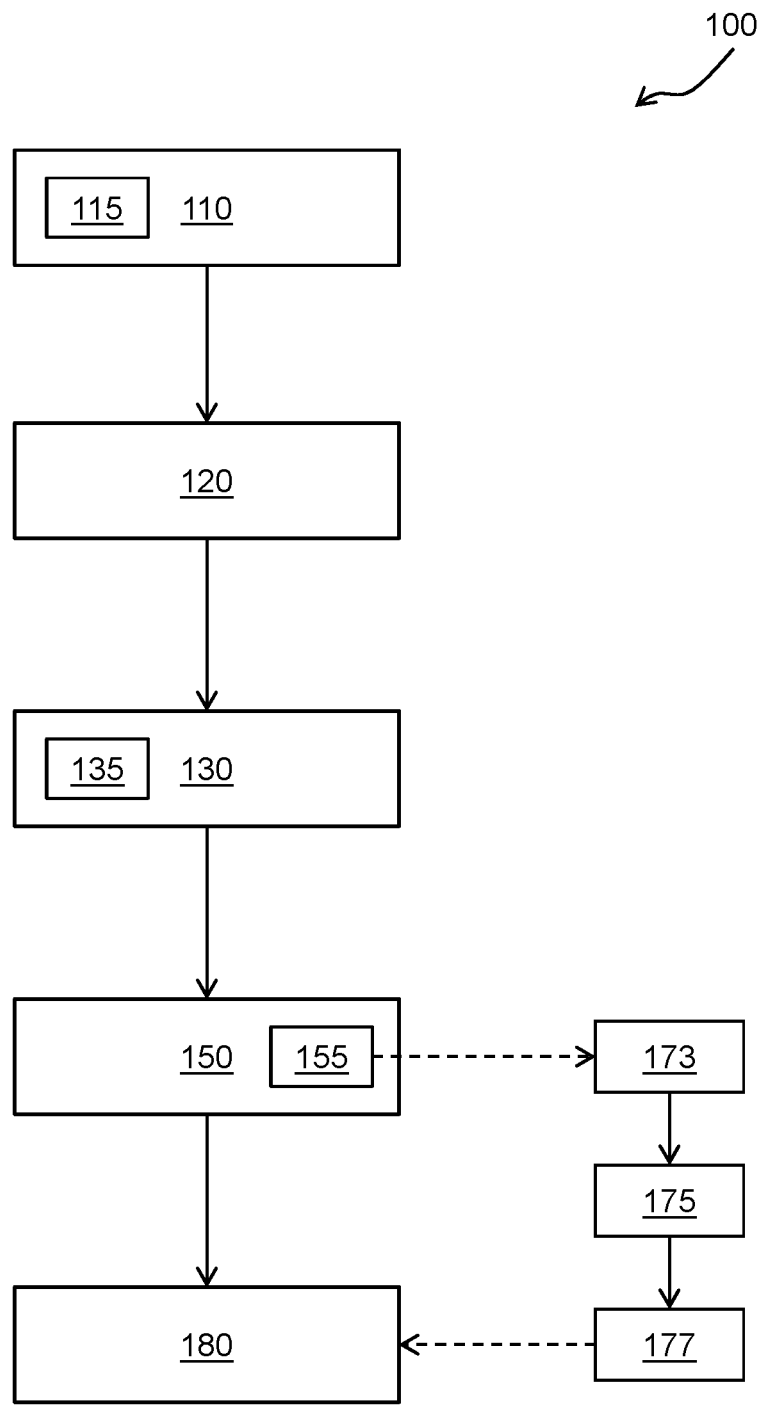
FIG. 1 depicts a method according to one or more embodiments.

Disclosed herein is a medical assessment method, device, and/or system. The medical assessment method, device, and/or system operates to provide identification, evaluation, and/or diagnosis of any condition or illness and proposing further evaluation. By way of example, the medical assessment method, device, and/or system is described herein, but not limited thereto, for diagnoses of neurological and other conditions.

The medical assessment method, device, and/or system can be practically applied as a stand-alone implementation in a discrete device (e.g., direct in-home medical evaluation tool), an augmentation/expansion package integrating into, layering on top of, and/or enhancing existing medical technology (e.g., supplemental software assisting electrocardiography (EKG) and other systems), and/or as a comprehensive multi-instance software across multiple devices connecting multiple users to deliver health and medical services (e.g., a telehealth or telemedicine environment). In all of these practically applied cases, the medical assessment method, device, and/or system can build, train, and utilize machine learning and/or an artificial intelligence (ML/AI) algorithms in support of the identifications, evaluations, and/or diagnoses of conditions or illnesses. Accordingly, the medical assessment method, device, and/or system can be embodied in a software platform (that generates an interface of graphic user interface (GUI)), as a computer program product that is necessarily rooted in at least one processor to improve operations of the at least one processor and a computer system or environment including the at least one processor.

According to one or more embodiments, the software platform described herein provides early identification and intervention of ischemic strokes without a need for skilled experts. Note that while early identification and intervention of ischemic strokes is discussed as an example application of the software platform, the software platform is further applicable for other medical assessments. One or more advantages, technical effects, and/or benefits of the software platform (e.g., the operating the methods herein) include, but are not limited to, integrating computer vision and sensor readings to automate and streamline medical assessments to address a lack of infrastructure and resources for clinicians or providers present; providing diagnosis and intervention of acute stroke patients, as well as post-stroke patients by automating complex time-consuming stroke evaluations; and objectively detecting a gain/loss of motor functions based on a physical exam history (of people at high risk of repeated stroke), which could serve as evidence for emergency room physicians in determining the presence of a newly developed motor deficiency.

As patients require immediate and comprehensive evaluations by skilled experts (e.g., a neurologist who evaluates for a stroke of a patient with a complex and nuanced neurological exam), so do the skilled experts require training and experience to perform (both well and correctly) the immediate and comprehensive evaluations. Training can be expensive and time consuming. Experience can be in limited supply (e.g., a number of patients far exceeds the neurologist available). Further, quality variations and diagnosis disparities of the immediate and comprehensive evaluations can occur between providers, which lead to poor outcomes for patients. Furthermore, real-world medical services and information have limited certainty (e.g., do not expressly track what is in a textbook), which leads to inconsistent care or even malpractice. The software platform solves the need for immediate and comprehensive evaluations without time intensive and cost prohibitive training and experience by being able to identify, evaluate, and/or diagnose infectious diseases, bacterial infections, viral infections, hereditary diseases (e.g., genetic and non-genetic hereditary diseases), dermatological conditions, deficiency diseases, neurological conditions, physiological diseases, physical conditions, and other conditions and illnesses, as well as detecting symptoms of any condition or illness and proposing a common diagnosis or further evaluation.

According to one or more embodiments, the software platform is applicable to examining a patient, diagnosing Horner's syndrome or other condition or illness, and proposing further work-up when the software platform finds ptosis (e.g., a slight drooping of an upper eyelid on an affected side), miosis (e.g., constriction of a pupil of an eye on the affected side, making the pupil appear smaller than a pupil of an unaffected side), anhidrosis (e.g., decreased sweating or absence of sweating on the affected side of the face), enophthalmos (e.g., an appearance of an affected eye being slightly sunken in), and/or other symptoms.

According to one or more embodiments, the software platform is applicable to examining a patient, diagnosing vitiligo or other condition or illness, and proposing further work-up when the software platform finds white skin patches (e.g., well-defined and milky-white under a Wood's lamp examination), patches that correspond to areas of depigmentation (e.g., typically occurring on sun-exposed areas, for example, hands, feet, arms, face, lips, etc.), and/or other symptoms.

According to one or more embodiments, the software platform is applicable to examining a patient, diagnosing Bell's palsy or other condition or illness, and proposing further work-up when the software platform finds a sudden unilateral facial weakness or paralysis with drooping of one side of a face, inability to close the eye, loss of facial expression (e.g., often with no other neurological deficits), and/or other symptoms.

According to one or more embodiments, the software platform is applicable to examining a patient, diagnosing Parkinson's disease or other condition or illness, and proposing further work-up when the software platform finds a resting tremor, bradykinesia (e.g., slowness of movement), muscle rigidity, postural instability (e.g., often with a shuffling gait), and/or other symptoms.

According to one or more embodiments, the software platform is applicable to examining a patient, diagnosing Koplik spots, measles or other condition or illness, and proposing further work-up when the software platform finds a fever, a cough, a coryza (e.g., runny nose), conjunctivitis (e.g., red eyes), small white spots with bluish-white centers on a bright red background inside the mouth (e.g., buccal mucosa), and/or other symptoms.

According to one or more embodiments, the software platform is applicable to examining a patient, diagnosing broken bone, sprained ligament, or other condition or injury, and proposing further work-up when the software platform finds a lack of mobility or range, preferencing (e.g., favoring balance on one leg over another), and/or other symptoms.

According to one or more embodiments, the software platform is applicable to examining a patient for a range of conditions/ailments/problems (e.g., from infectious, to neurologic, to dermatologic, etc.) across a full scope of medical conditions. Thus, the software platform can identify a first patient concern while excluding other possible patient concerns based upon the findings of the software platform. By way of example, because bell's palsy is usually unilateral facial weakness and stroke can present similarly to bell's palsy, the software platform can operate to determine one condition vs the other (e.g., if forehead muscles are not weak, then stroke should be considered; if the forehead muscles are weak, then bell's palsy should be considered). Further, the software platform can also consider both conditions in parallel so that nuances across the full scope of medical conditions are analyzed.

One or more advantages, technical effects, and/or benefits of the software platform (e.g., the operating the methods herein) include, but are not limited to, integrating computer vision and sensor readings to automate and streamline medical assessments to address a lack of infrastructure and resources for clinicians or providers present; providing diagnosis and intervention; and objectively detecting a gain/loss of motor functions based on a physical exam history, which could serve as evidence for a need for emergency medical care.

As shown in FIG. 1, an exemplary method 100 of the software platform is illustrated according to one or more embodiments. The exemplary method 100 is for neurological assessment and can be stored on a memory as processor executable instructions. Note that a display, a second display, an audio output, a camera, a microphone, a light detecting and ranging (LIDAR) device, a communications device, and a processor are operably coupled to the memory so that the software platform can utilize these components to implement the exemplary method 100, when the processor is executing the processor executable instructions.

The exemplary method 100 begins at block 110, where the software platform prompts a patient to perform at least one of a plurality of actions. The prompting of the patient can include providing at least one patient prompt. The software platform can provide the at least one patient prompt via the display and/or through the audio output.

According to one or more embodiments, as shown in sub-block 115, the software platform can communicate with other devices or systems. The software platform can communicate with the display, the second display, the audio output, and/or the LIDAR device. For example, the software platform can communicate to the display or a second display and utilize the display or the second display to present at least a first portion of the at least one patient prompt. Further, the software platform can communicate to the audio output and utilize the audio output to produce/present at least a second portion of the at least one patient prompt. The software platform can communicate the first and second portions to a clinician facilitating the neurological assessment and/or to the patient receiving the neurological assessment.

At block 120, the software platform records video and/or audio of the at least one of a plurality of actions from the patient via the camera and/or the microphone. Further, the software platform can utilize the LIDAR device to obtain LIDAR data. The video, the audio, and/or the LIDAR data (e.g., recordings) can be obtained and recorded as non-standardized patient specific information. These recordings can be extensive in time, for example, totaling over fifteen (15) minutes.

At block 130, the software platform generates one or more relevant clipped portions from the video and the audio. According to one or more embodiments, as shown in sub-block 135, the software platform generates the one or more relevant clipped portions from the video, the audio, and/or the LIDAR data. The software platform can utilize one or more ML/AI algorithms, as described herein, to clip only to 'relevant' portions of the recordings. These clipped portions are discrete targeted standardized data. Targeted standardized data may be, for example, a clipped portion of audio and/or video totaling two (2) to twelve (12) seconds of the recording (e.g., showing just a portion of a video relative to prompt). One or more advantages, technical effects, and/or benefits of the clipped portions of the software platform (over the extensive non-standardized recordings) include providing the clipped portions for rapid evaluation or reviewing, thereby reducing processing time and processing operations of the clipped portions.

The one or more relevant clipped portions are a conversion of the non-standardized patient specific information into standardized patient specific information. Examples of the patient specific information include, but are not limited to, a level of consciousness response, a best gaze response, a visual response, a facial palsy response, a motor arm response, a motor leg response, a limb ataxia response, a sensory response, a best language response, a dysarthria response, and an extinction and inattention response. Thus, the patient specific information can start in a non-standardized form and be converted into a standardized form.

The non-standardized patient specific information for the level of consciousness response can include the video, the audio, and/or the LIDAR recordings for an alertness and responsiveness of a patient. One or more relevant clipped portions are generated from these recording to include one or more audio responses by a patient to one or more questions. Example questions include, but are not limited to, 'What is the current month?', 'How old are you?', and 'Close and open your eyes and grasping and releasing a hand patient'.

The non-standardized patient specific information for the best gaze response can include the video, the audio, and/or the LIDAR recordings for an ability to follow an object with their eyes. One or more relevant clipped portions are generated from these recordings to include images of a patient moving their eyes in response to one or more prompts. Example prompts include, but are not limited to, asking the patient to follow an object horizontally.

The non-standardized patient specific information for the visual field response can include the video, the audio, and/or the LIDAR recordings for an ability to see in all directions by a patient. One or more relevant clipped portions are generated from these recordings to include images of a patient demonstrating visual field of the patient in response to one or more prompts (e.g., video confirming the patient can see things that are not directly in front of them).

The non-standardized patient specific information for the facial palsy response can include the video, the audio, and/or the LIDAR recordings for an ability to move a face of/by a patient. One or more relevant clipped portions are generated from these recordings to include images of a patient demonstrating ability to move facial muscles in response to one or more prompts. Example prompts include, but are not limited to, asking the patient to show teeth or raise eyebrows while closing their eyes. Further, if the patient is not responsive, the prompts can include a noxious stimuli (e.g., a bad smell) and observing the facial reaction.

The non-standardized patient specific information for the motor arm response can include the video, the audio, and/or the LIDAR recordings for an ability to move an arm of/by a patient. One or more relevant clipped portions are generated from these recordings to include images of a patient demonstrating ability to hold arms in one or more upright positions for a certain amount of time. Example prompts include, but are not limited to, asking the patient to hold each arm, in turn, at a 90-degree angle (e.g., if sitting) or 45-degree angle (e.g., if supine), palms up.

The non-standardized patient specific information for the motor leg response can include the video, the audio, and/or the LIDAR recordings for an ability to move a leg of/by a patient. One or more relevant clipped portions are generated from these recordings to include images of a patient demonstrating an ability to hold each leg in one or more upright positions for a certain amount of time. Example prompts include, but are not limited to, asking the patient to hold each leg up at 30 degrees.

The non-standardized patient specific information for the limb ataxia response can include the video, the audio, and/or the LIDAR recordings for an ability to coordinate limb movement of/by a patient. One or more relevant clipped portions are generated from these recordings to include images of a patient demonstrating ability to pass a finger-nose-finger and heel-shin test on both sides.

The non-standardized patient specific information for the sensory response can include the video, the audio, and/or the LIDAR recordings for an ability to feel by a patient. One or more relevant clipped portions are generated from these recordings to include images of a patient demonstrating ability to sense a pinprick and a noxious (e.g., unpleasant) stimuli.

The non-standardized patient specific information for the best language can include the video, the audio, and/or the LIDAR recordings for an ability to understand and speak by a patient. One or more relevant clipped portions are generated from these recordings to include images of a patient demonstrating whether a stroke affected language abilities of the patient. Example prompts include, but are not limited to, asking the patient to hold each leg up at 30 degrees and asking the patient to describe the situation in a picture.

The non-standardized patient specific information for the dysarthria response can include the video, the audio, and/or the LIDAR recordings for an ability to speak by a patient. One or more relevant clipped portions are generated from these recordings to include images of a patient demonstrating whether there is slurring in a speech of the patient.

The non-standardized patient specific information for the extinction and inattention response can include the video, the audio, and/or the LIDAR recordings for an ability to pay attention and detect objects on one side of a body of/by a patient. For instance, one or more relevant clipped portions of all previous tests can be used to infer the extinction and inattention response.

At block 150, the software platform causes a determination of a neurologic status for the patient based on the standardized patient specific information.

The software platform can cause the determination internally to generate the analysis result that includes the neurologic status. According to one or more embodiments, the software platform can utilize the standardized patient specific information to assess a severity of a stroke. According to one or more embodiments, the software platform can utilize the standardized patient specific information to track a progress of a patient over time. In this regard, the one or more relevant clipped portions are further utilized to generate additional standardized patient specific information represented by a degree of abnormality. The degree of abnormality of the software platform is a unique parameter for the software platform that standardizes the disparate, non-standardized data received and recorded by the software platform. The degree of abnormality, practically, identifies an amount of deviation of patient conditions from expected normal patient responses. The degree of abnormality can be provided as one or more scores or sub-scores (or averages or derivations thereof) on one or more scales (e.g., the NIH Stroke Scale/Score (NIHSS) that quantifies stroke severity based on weighted evaluation findings). The scores or sub-scores are determined from one or more tests (e.g., a series of tests) that evaluate patient specific information within the one or more relevant clipped portions (e.g., the level of consciousness response, the best gaze response, the visual response, the facial palsy response, the motor arm response, the motor leg response, the limb ataxia response, the sensory response, the best language response, the dysarthria response, and the extinction and inattention response).

The standardized patient specific information for the level of consciousness can include a scale and/or a score for each of the one or more responses by the patient to the one or more questions of the level of consciousness (e.g., the scale and score identifies the level of alertness and responsiveness).

The standardized patient specific information for the best gaze can include a scale and/or a score that evaluates possible damage to an ability to move their eyes normally.

The standardized patient specific information for the visual response can include a scale and/or a score for the patient performance with respect to upper and lower quadrants of the visual field.

The standardized patient specific information for the facial palsy response can include a scale and/or a score for each of the one or more responses by the patient to the one or more prompt to show teeth or raise eyebrows while closing eyes.

The standardized patient specific information for the motor arm response can include a scale and/or a score for arm movement (e.g., a score of zero (0) can be considered a best score or a worst score, depending on the configuration, where a patient can or cannot hold up arms for at least 10 seconds without drift).

The standardized patient specific information for the motor leg response can include a scale and/or a score for leg movement (e.g., a score of zero (0) can be considered a best score or a worst score, depending on the configuration, where a patient can or cannot hold up arms for at least 5 seconds).

The standardized patient specific information for the limb ataxia response can include a scale and/or a score indicating whether there was damage in the brain, for example, the cerebellum.

The standardized patient specific information for the sensory response can include a scale and/or a score indicating a level of response.

The standardized patient specific information for the best language response can include a scale and/or a score for loss of fluency, limitations on ideas that can be expressed, and other elements (e.g., used to evaluate the level of aphasia or speech/language impairment).

The standardized patient specific information for the dysarthria response can include scoring a scale and/or a score respective to slurring of speech.

The standardized patient specific information for the extinction and inattention response can include a scale and/or a score indicating a level of attention a patient pays to their environment, as well as sensory abilities in each of the five senses.

The software platform can also cause the determination by transmitting the one or more relevant clipped portions to a second system for analysis. The software platform can utilize the communications device transmit information to and receive information from the second system. According to one or more embodiments, as shown in sub-block 155, the software platform can utilize the communications device to transmit the one or more relevant clipped portions to the second system. At block 173, the second system can receive the one or more relevant clipped portions from the software platform. At block 175, the second system can analyze the one or more relevant clipped portions to generate the analysis result (as described with respect to the software platform). According to one or more embodiments, a software instance of the second system performs the analysis of the one or more relevant clipped portions to generate the analysis result. According to one or more embodiments, a user (e.g., a clinician, a technician, or a doctor) can interact with the software instance of the second system to perform the analysis of the one or more relevant clipped portions to generate the analysis result. At block 177, the second system can transmit the analysis result to the software platform.

At block 180, the software platform receives the analysis result. The analysis result can include the neurologic status. According to one or more embodiments, the neurologic status can be a data set, which includes at least the standardized patient specific information, that details whether a condition is identified and/or diagnosed and further evaluation and/or treatment is proposed. The neurologic status can be presented in one or more GUIs of the software platform, for example, that include red interface elements for a stroke diagnosis or green interface elements for a normal diagnosis associated with the standardized patient specific information.

Figure 2:
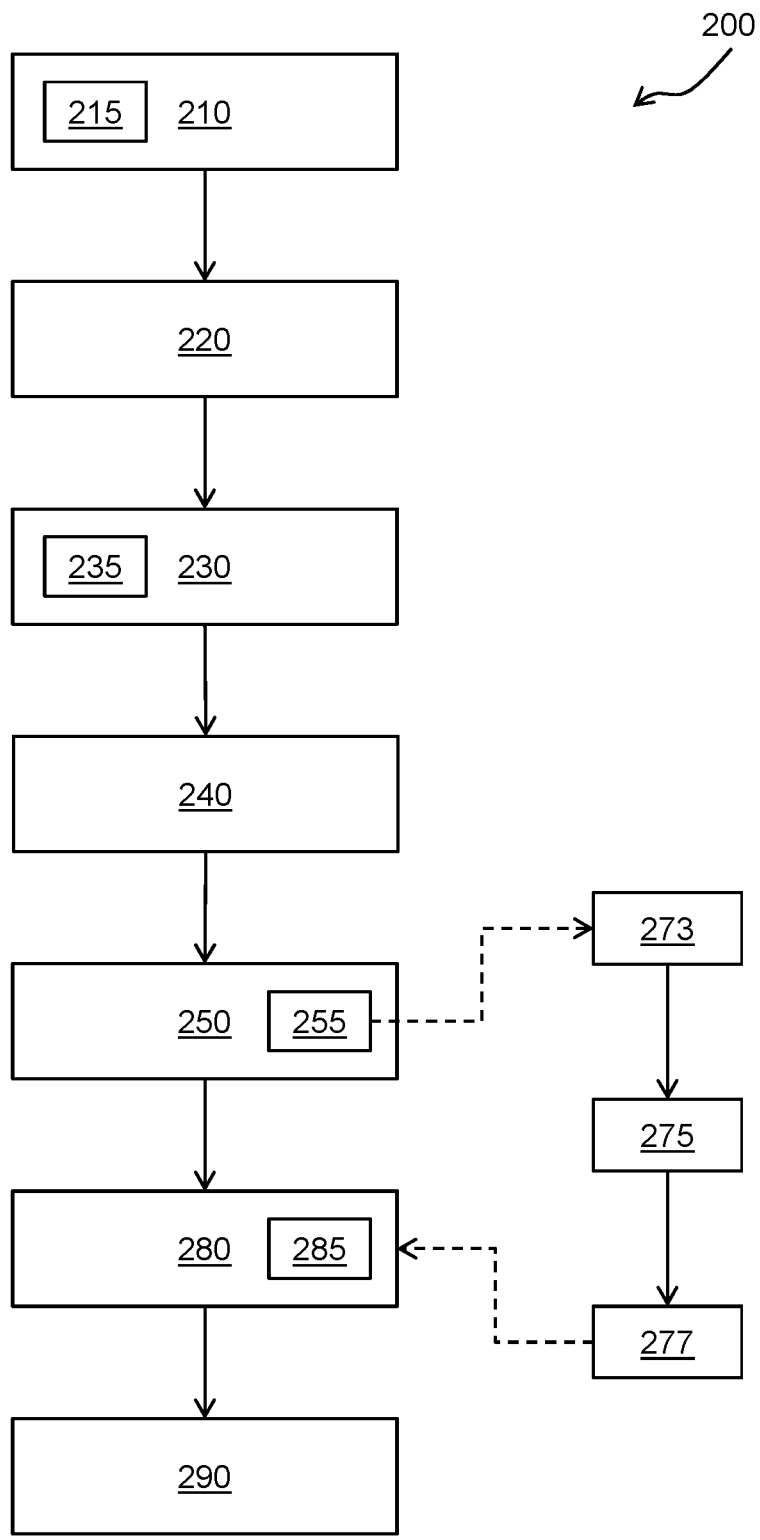
FIG. 2 depicts a method according to one or more embodiments.

As shown in FIG. 2, an exemplary method 200 of the software platform is illustrated according to one or more embodiments. The exemplary method 200 is for neurological assessment and can be stored on a memory as processor executable instructions. Note that a display, a second display, an audio output, a camera, a microphone, a LIDAR device, a communications device, and a processor are operably coupled to the memory so that the software platform can utilize these components to implement the exemplary method 200, when the processor is executing the processor executable instructions.

The exemplary method 200 begins at block 210, where the software platform prompts a patient to perform at least one of a plurality of actions. The prompting of the patient can include providing at least one patient prompt. The software platform can provide the at least one patient prompt via the display and/or through the audio output.

According to one or more embodiments, as shown in sub-block 215, the software platform can communicate with other devices or systems. The software platform can communicate with the display, the second display, the audio output, and/or the LIDAR device. For example, the software platform can communicate to the display or a second display and utilize the display or the second display to present at least a first portion of the at least one patient prompt. Further, the software platform can communicate to the audio output and utilize the audio output to produce/present at least a second portion of the at least one patient prompt. The software platform can communicate the first and second portions to a clinician facilitating the neurological assessment and/or to the patient receiving the neurological assessment.

At block 220, the software platform records video and/or audio of one or more of the plurality of actions from the patient via the camera and/or the microphone. Further, the software platform can utilize the LIDAR device to obtain LIDAR data, which includes the one or more of the plurality of actions. The video, the audio, and/or the LIDAR data can be obtained and recorded as non-standardized patient specific information.

At block 230, the software platform generates one or more relevant clipped portions from the video and the audio. According to one or more embodiments, as shown in sub-block 235, the software platform generates the one or more relevant clipped portions from the video, the audio, and/or the LIDAR data. The one or more relevant clipped portions can include a conversion of the non-standardized patient specific information into standardized patient specific information. The software platform can utilize one or more ML/AI algorithms, as described herein, to clip only to 'relevant' portions of the recordings.

At block 240, the software platform processes the one or more relevant clipped portions of the video and the audio to produce a neurological assessment score for the patient. A neurological assessment score is an example implementation of assessing a degree of abnormality. The neurological assessment score (and any sub-scores described herein) can be zero (0) or any integer selected from a range of one (1) to one hundred (100). For example, a high score can be ninety-seven (97), while a low score would be two (2).

At block 250, the software platform determines a neurologic status for the patient based on the neurological assessment score. The neurologic status can be determined within the software platform. According to one or more embodiments, the neurologic status is a data set, which includes at least the neurological assessment score, that details whether a condition is identified and/or diagnosed and further evaluation and/or treatment is proposed. The neurologic status can be presented in one or more GUIs of the software platform, for example, that include red interface elements for a stroke diagnosis or green interface elements for a normal diagnosis associated with the neurological assessment score.

According to one or more embodiments, the software platform can utilize a second system to determine the neurologic status. In this regard, the software platform can utilize the communications device transmit information to and receive information from the second system. As shown in sub-block 255, the software platform can utilize the communications device to transmit the one or more relevant clipped portions to the second system. At block 273, the second system can receive the one or more relevant clipped portions from the software platform. At block 275, the second system can analyze the one or more relevant clipped portions to generate the analysis result. At block 277, the second system can transmit the analysis result to the software platform. At block 285, the software platform receives the analysis result. The analysis result can include the neurologic status.

At block 290, the software platform implements one or more neurological responses based on the neurologic status. Example of the one or more neurological responses can include, but is not limited to, take no action, order physiological tests, order imaging tests, order suspected condition tests, and implement/initiate interventions, for example, administration of medication, procedures, surgeries, and other interventions. Note that the one or more neurological responses are representative of a larger range reactive actions, initiatives, and/or recommendations by the software platform to facilitate proper care for the user/patient. According to one or more embodiments, the one or more neurological responses can include different and/or overlapping response for each patient (e.g., a first patient may not require any tests and may need to proceed directly to surgery, a second patient may require a physiologic test but not an imaging test, a third patient may require a physiologic test and an imaging test, etc.).

According to one or more embodiments, and in practical application of the methods 100 and 200 herein, the software platform provides immediate evaluation and consideration of treatment for symptomatic strokes to decrease long term sequelae including disability caused thereby. To achieve this end, the software platform overcomes the evaluation and treatment problems of conventional technology by automatically recognizing for a patient or another person that a stroke is, or may be occurring; timely and accurately evaluating an emergency need; rapidly determining a treatment need, if any; reduce or eliminate a requirement for extensive neurological experience; provide rapid accurate assessments; eliminate variability of clinical exams and recommendations; eliminate inconsistent utilization of treatment despite supportive evidence (e.g., exam data, historical data, imaging data, etc.); minimize healthcare provider tasks; and provide a standardized tool across cultures, languages, and societies that lead to better patient outcomes.

Figure 3:
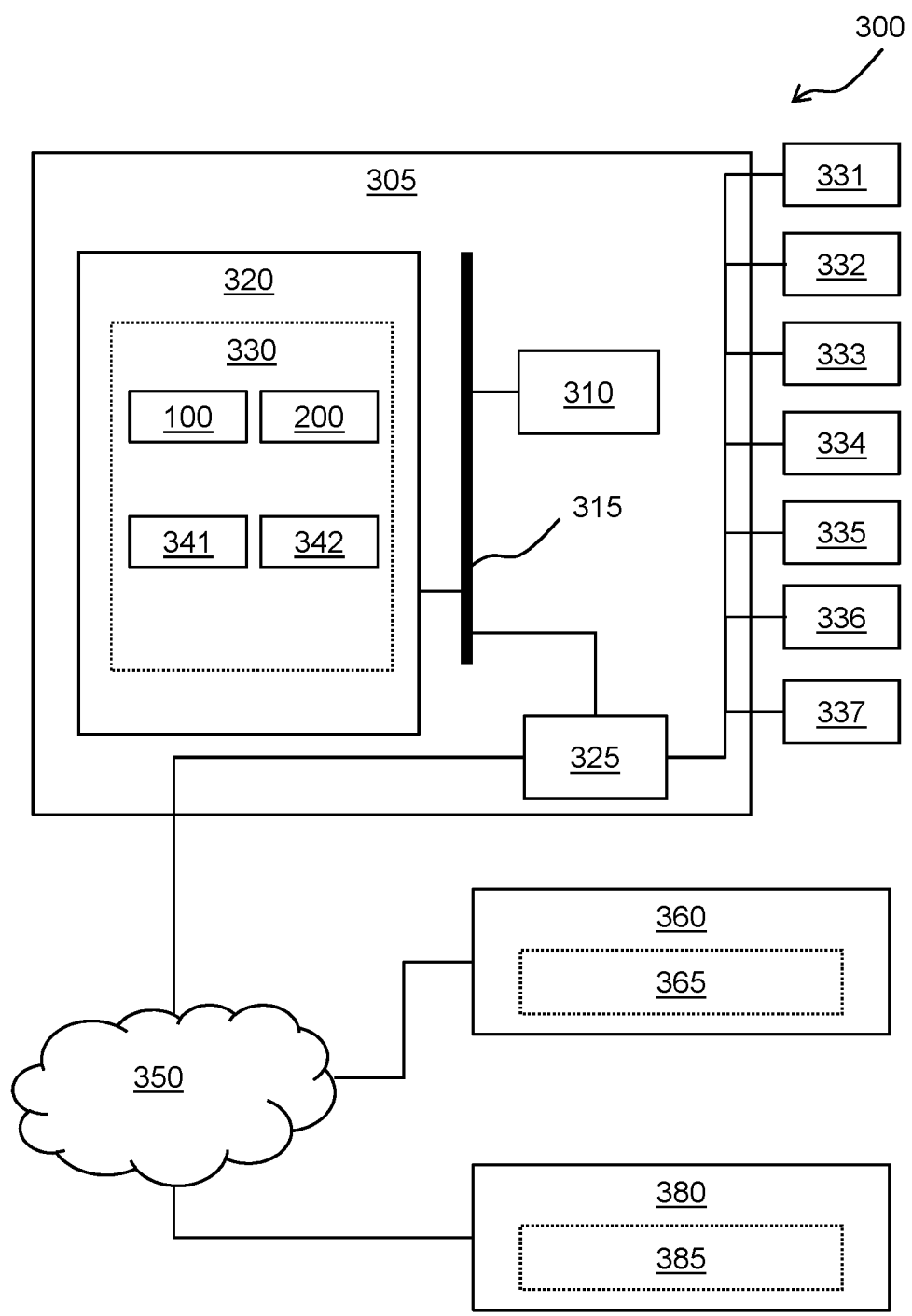
FIG. 3 depicts a system according to one or more embodiments.

Turning now to FIG. 3, a computing system 300 is illustrated according to one or more embodiments. The computing system 300 can be representative of any computing device, computing apparatus, and/or computing environment, which comprise hardware, software, or a combination thereof. Further, embodiments of the computing system 300 disclosed may include apparatuses, systems, methods, and/or computer program products at any possible technical detail level of integration.

The computing system 300 has a device 305 with one or more central processing units (CPU(s)), which are collectively or generically referred to as a processor 310. The processor 310, also referred to as processing circuits, is coupled via a system bus 315 to a system memory 320 and various other components.

The computing system 300 and/or the device 305 may be adapted or configured to perform as an online platform, a server, an embedded computing system, a personal computer, a console, a personal digital assistant (PDA), a cell phone, a tablet computing device, a quantum computing device, cloud computing device, a mobile device, a smartphone, a fixed mobile device, a smart display, a wearable computer, a robotic or other humanoid device, a robot, or other device. According to one or more embodiments, the device 305 can be practically applied as a stand-alone implementation in a discrete device (e.g., direct in-home medical evaluation tool).

The processor 310 may be any type of general or specific purpose processor, including a central processing unit (CPU), application specific integrated circuit (ASIC), field programmable gate array (FPGA), graphics processing unit (GPU), controller, multi-core processing unit, three dimensional processor, quantum computing device, or any combination thereof. The processor 310 may also have multiple processing cores, and at least some of the cores may be configured to perform specific functions. Multi-parallel processing may also be configured.

The bus 315 (or other communication mechanism) is configured for communicating information or data to the processor 310, the system memory 320, and various other components, for example at least an adapter 325. According to one or more embodiments, the various other components can include, but are not limited to one or more displays 331 (e.g., a display and a second display), an audio output 333, a camera 334, a microphone 335, a LIDAR device 335, a communications device (as represented by the adapter 325), and other input/output devices 336 (e.g., an electrode 337) and transducers that detect and convert environmental conditions into electrical signals.

The system memory 320 is an example of a (non-transitory) computer readable storage medium, where software 330 (i.e., the software platform described herein) can be stored as software components, modules, engines, instructions, or other code for execution by the processor 310 to cause the device 305 and/or the computing system 300 to operate, for example, described herein with reference to FIGS. 1-2. The system memory 320 can include any combination of a read only memory (ROM), a random access memory (RAM), internal or external Flash memory, embedded static-RAM (SRAM), solid-state memory, cache, static storage, or any other types of volatile or non-volatile memory. Non-transitory computer readable storage mediums may be any media that can be accessed by the processor 310 and may include volatile media, non-volatile media, or other media. For example, the ROM is coupled to the system bus 315 and may include a basic input/output system (BIOS), which controls certain basic functions of the device 305, and the RAM is read-write memory coupled to the system bus 315 for use by the processors 310. Non-transitory computer readable storage mediums can include any media that is removable, non-removable, or other media.

According to one or more embodiments, the software 330 can be configured in hardware, software, or a hybrid implementation. The software 330 can be composed of modules and/or models that are in operative communication with one another, and to pass information or instructions. The software 330 of FIG. 3 can also be representative of an operating system, a mobile application, a client application, and/or other application for the device 305 for the computing system 300. According to one or more embodiments, the software 330 can be practically applied as an augmentation/expansion package integrating into, layering on top of, and/or enhancing existing medical technology (e.g., supplemental software assisting electrocardiography (EKG) and other systems).

According to one or more embodiments, the software 330 can provide one or more user interfaces, for example, on behalf of the operating system or other application and/or directly as needed. The user interfaces include, but are not limited to, graphic user interfaces, window interfaces, internet browsers, and/or other visual interfaces for applications, operating systems, file folders, and other applications/systems. Thus, user activity can include any interaction or manipulation of the user interfaces provided by the software 330. The software 330 can further include custom modules to perform application specific processes or derivatives thereof, such that the computing system 300 may include additional functionality. For example, according to one or more embodiments, the software 330 may be configured to store information, instructions, commands, or data to be executed or processed by the processor 310 to logically implement the exemplary method 100 of FIG. 1 and/or the exemplary method 200 of FIG. 2 (as represented by blocks 100 and 200 within the software 330). Thus, by way of example, the system memory 320 including the software 330 as processor executable instructions can be included in the device 305 (e.g., a machine), which also includes the display 331, the camera 334, the audio output 333, the microphone 335, and the processor 310, and the device can perform any of the methods described herein.

According to one or more embodiments, the software 330 enables custom artificial intelligence (AI) to provide seamless medical expertise, diagnosis, instruction, and guidance. According to one or more embodiments, the software 330 may be configured to store information, instructions, commands, or data to be executed or processed by the processor 310 to logically implement the exemplary methods 100 and 200 of FIGS. 1-2. The software 330 can be implemented as a computer program product that is necessarily rooted in at least the one processor 310 to improve operations of the device 305 and/or the computer system 300.

One or more advantages, technical effects, and/or benefits of the software 330 (e.g., the software platform operating the methods herein) include, but are not limited to, integrating computer vision and sensor readings to automate and streamline medical assessments to address a lack of infrastructure and resources for clinicians or providers.

One or more advantages, technical effects, and/or benefits of the software 330 (e.g., the software platform operating the methods herein) include, but are not limited to, providing diagnosis and intervention of acute stroke patients, as well as post-stroke patients by automating complex time-consuming stroke evaluations.

One or more advantages, technical effects, and/or benefits of the software 330 (e.g., the software platform operating the methods herein) include, but are not limited to, objectively detecting a gain/loss of motor functions based on a physical exam history (of people at high risk of repeated stroke), which could serve as evidence for emergency room physicians in determining the presence of a newly developed motor deficiency.

One or more advantages, technical effects, and/or benefits of the software 330 (e.g., the software platform operating the method herein) include, but are not limited to, adapting to multiple stroke evaluation scales thereby eliminating required time and training for nursing and other healthcare professionals. By way of example, patients who arrive at the emergency room within three (3) hours of first symptoms of a stroke often have less disability three (3) months after the stroke than those who received delayed care. The software platform, which provides stroke identification and clinical evaluation, can identify the stroke within the three (3) hours of first symptoms without clinicians or providers present.

One or more advantages, technical effects, and/or benefits of the software 330 (e.g., the software platform operating the methods herein) include, but are not limited to, providing efficient diagnosing from the generated standardized patient specific information to increase an effectiveness of initial treatment, as well as subsequent recovery.

According to one or more embodiments, the software 330 implements a user interface 341 including one or more elements that collectively prompt, obtain, organize, and present data 342. The data 342 can include, but is not limited to, non-standardized patient specific information and standardized patient specific information. Example of the data include one or more neurological assessments, one or more actions, one or more patient prompts, video data, audio data, LIDAR data, one or more relevant clipped portions, level of consciousness responses, best gaze responses, visual responses, facial palsy responses, motor arm responses, motor leg responses, limb ataxia responses, sensory responses, best language responses, dysarthria responses, extinction and inattention responses, one or more analysis result, one or more scores (e.g., one or more neurological assessment scores), one or more neurologic statuses, one or more neurological responses, patient communications, clinician communications, provider communications, other non-standardized patient specific information, and other standardized patient specific information.

Further, modules and/or models of the software 330 can be implemented as a hardware circuit comprising custom very large scale integration (VLSI) circuits or gate arrays, off-the-shelf semiconductors for example, logic chips, transistors, or other discrete components, in programmable hardware devices (e.g., field programmable gate arrays, programmable array logic, programmable logic devices), graphics processing units, or other logic. Modules and/or models of the software 330 can be at least partially implemented in software for execution by various types of processors. According to one or more embodiments, an identified unit of executable code may include one or more physical or logical blocks of computer instructions that may, for instance, be organized as an object, procedure, routine, subroutine, or function. Executables of an identified module co-located or stored in different locations such that, when joined logically together, comprise the module. A module of executable code may be a single instruction, one or more data structures, one or more data sets, a plurality of instructions, or other instructions distributed over several different code segments, among different programs, across several memory devices, or other devices. Operational or functional data may be identified and illustrated herein within modules of the software 330, and may be embodied in a suitable form and organized within any suitable type of data structure.

Furthermore, modules and/or models of the software 330 can also include, but are not limited to, location modules and machine learning and/or an artificial intelligence (ML/AI) algorithm modules. A location module can be configured to create, build, store, and provide algorithms and models that determine a location of the device 305 and relative distances to clinicians or providers. According to more or more embodiments, the location module can implement location, geosocial networking, spatial navigation, satellite orientation, surveying, distance, direction, and/or time software.

A ML/AI algorithm module can be configured to create, build, store, and provide algorithms and models that improve automatically through experience, as well as emulate 'natural' cognitive abilities of humans. In an example, machine learning software uses training data to build a particular model and to improve that model, while artificial intelligence software perceives an environment (e.g., receives the non-standard patient specific information) and takes actions (e.g., makes neurological assessments) to solve a problem and/or produce an output.

In general, ML/AI of the software 330 operates with respect to the hardware, using the data, to train a machine, build a model, and predict outcomes. For instance, the machine of software 330 operates as a software controller executing on the hardware. Data (e.g., the data as described herein) can be on-going data (i.e., data that is being continuously collected) or output data associated with the hardware. The data can also include currently collected data (e.g., the non-standardized patient specific information, the standardized patient specific information, the video/audio/LIDAR recordings, the one or more relevant clipped portions, etc.), historical data, or other data from the hardware; and can be related to the hardware. The data can be divided by the machine into one or more subsets. Further, the machine trains, which can include an analysis and correlation of the data collected. For example, in the case of the medical assessments, the data of a patient pool may be trained to determine if a correlation or link exists between certain observed conditions of the patient and the outcome. In accordance with another embodiment, training the machine can include self-training utilizing the one or more subsets. In this regard, for example, the machine learns to detect case classifications on a point by point basis. Moreover, the model is built on the data. Building the model can include physical hardware or software modeling, algorithmic modeling, and/or the like that seeks to represent the data (or subsets thereof) that has been collected and trained. In some aspects, building of the model is part of self-training operations by the machine. The model can be configured to model the operation of hardware and model the data collected from the hardware to predict the outcome achieved by the hardware. Predicting the outcomes (of the model associated with the hardware 450) can utilize a trained model. Thus, using the outcome that is predicted, the machine, the model, and the hardware can be configured accordingly.

For the ML/AI of the software 330 to operate as described, the ML/AI algorithm module therein can include neural networks. In general, a neural network is a network or circuit of neurons, or in a modern sense, an artificial neural network (ANN), composed of artificial neurons or nodes or cells. Neural networks are non-linear statistical data modeling or decision-making tools that can be used to model complex relationships between inputs and outputs or to find patterns in data. Thus, ANNs may be used for predictive modeling for medical assessment and adaptive control applications, while being trained via a dataset. Note that self-learning resulting from experience can occur within ANNs, which can derive conclusions from a complex and seemingly unrelated set of information. The utility of ANN models lies in the fact that ANN models can be used to infer a function from observations and also to use that function.

Unsupervised neural networks can also be used to learn representations of the input that capture salient characteristics of the input distribution, and more recently, deep learning algorithms, which can implicitly learn the distribution function of the observed data. Learning in neural networks is particularly useful in applications where the complexity of the data (e.g., the non-standardized patient specific information, the standardized patient specific information, the video/audio/LIDAR recordings, the one or more relevant clipped portions, historical data, etc.) or task (e.g., identification, evaluation, and/or diagnosis of any condition or illness and proposing further evaluation) makes the design of such functions by hand or by human action impractical or impossible.

For the ML/AI system, ML/AI algorithms therein can include neural networks that are divided generally according to tasks to which they are applied. These divisions tend to fall within the following categories: regression analysis (e.g., function approximation) including time series prediction and modeling; classification including pattern and sequence recognition; novelty detection and sequential decision making; data processing including filtering; clustering; blind signal separation, and compression. According to one or more embodiments, the neural network can implement a long short-term memory neural network architecture, a convolutional neural network (CNN) architecture, or other the like. The neural network can be configurable with respect to a number of layers, a number of connections (e.g., encoder/decoder connections), a regularization technique (e.g., dropout); and an optimization feature.

With respect to the adapter 325 of FIG. 3, the device 305 can particularly include an input/output (I/O) adapter, a device adapter, and/or a communications adapter. According to one or more embodiments, the I/O adapter can be configured as a small computer system interface (SCSI), of in view of frequency division multiple access (FDMA) single carrier FDMA (SC-FDMA), time division multiple access (TDMA), code division multiple access (CDMA), orthogonal frequency-division multiplexing (OFDM), orthogonal frequency-division multiple access (OFDMA), global system for mobile (GSM) communications, general packet radio service (GPRS), universal mobile telecommunications system (UMTS), cdma2000, wideband CDMA (W-CDMA), high-speed downlink packet access (HSDPA), high-speed uplink packet access (HSUPA), high-speed packet access (HSPA), long term evolution (LTE), LTE Advanced (LTE-A), 802.11x, Wi-Fi, Zigbee, Ultra-WideBand (UWB), 802.16x, 802.15, home Node-B (HnB), Bluetooth, radio frequency identification (RFID), infrared data association (IrDA), near-field communications (NFC), fifth generation (5G), new radio (NR), or any other wireless or wired device/transceiver for communication.

The device adapter interconnects the input/output devices 336 to the system bus 315, for example the one or more displays 331, the audio output 333 (e.g., a speaker), the camera 334, the microphone 335, the LIDAR device 335, the electrode 337, a keyboard, a control device, or other devices.

The electrode 337 can be any transducer or set of electrical components that detect and convert environmental conditions into electrical signals (e.g., data for storage and consumption by the software 330). By way of example, the electrode 337 can generate an electric field to detect disturbance therein caused by objects or a phenomenon. The electrode 337 can stimulate a patient through vibration, an electrical shock, heat, or other stimuli while the camera 334, the microphone 335, and/or the LIDAR device 335 records a response (e.g., patient participation) or lack of response (e.g., deficiency in a level of consciousness). According to one or more embodiments, the electrode 337 can be representative of one or more of a studded vibrating tape (e.g., an adhesive, single stripe, studded electrode), a grip electrodes that a patient holds and squeezes to grade strength, and a needle electrode that determines muscle activation. The electrode 337 can be attached or in proximity to a patient while being wired or connected wirelessly (e.g., by Zigbee, Bluetooth, near-field communications (NFC), etc. as described herein) to the device 305.

The one or more displays 331 one or more displays 331 can be configured to provide one or more user interfaces or GUIs (e.g., the user interface 341) of the software 330, as the users interact with the device 305. Examples of the one or more displays 331 can include, but are not limited to, a plasma, a liquid crystal display (LCD), a light emitting diode (LED), a field emission display (FED), an organic light emitting diode (OLED) display, a flexible OLED display, a flexible substrate display, a projection display, a 4K display, a high definition (HD) display, a Retina© display, an in-plane switching (IPS) display or other display. The one or more displays 331 may be configured as a touch, three dimensional (3D) touch, multi-input touch, or multi-touch display using resistive, capacitive, surface-acoustic wave (SAW) capacitive, infrared, optical imaging, dispersive signal technology, acoustic pulse recognition, frustrated total internal reflection, or other technology as understood by one of ordinary skill in the art for input/output (I/O).

The keyboard and the control device, for example, a computer mouse, a touchpad, a touch screen, a keypad, or other device, may be further coupled to the system bus 315 for input to the device 305. One or more inputs (e.g., the video, the audio, and/or the LIDAR data) may be provided to the device 305 by the camera 334, the microphone 335, and the LIDAR device 335. In addition, one or more inputs may be provided to the computing system 300 remotely via another computing system in communication therewith, or the device 305 may operate autonomously.

The communications adapter (e.g., the communications device) interconnects the system bus 315 with a network 350, which may be an outside network, enabling the device 305 to communicate data with other devices through the network 350 (e.g., for example, a remote device 360 and/or a cloud device 370). In one embodiment, the adapter 325 may be connected to one or more I/O buses that are connected to the system bus 315 via an intermediate bus bridge. Suitable I/O buses for connecting peripheral devices for example, hard disk controllers, network adapters, and graphics adapters typically include common protocols, for example, the Peripheral Component Interconnect (PCI).

According to one or more embodiments, the functionality of the device 305 with respect to the software 330 can also be implemented on the remote device 360 and/or the cloud device 370, as represented by separate instances 380 and 390 of the software 330. According to one or more embodiments, the computing system 300 can be practically applied as a comprehensive multi-instance software across multiple devices connecting multiple users to deliver health and medical services (e.g., a telehealth or telemedicine environment). Note that the data 342 can be stored in a common repository located at the device 305, remote device 360, and/or the cloud device 370 and can be downloaded (on demand) to and/or from each of the device 305, remote device 360, and/or the cloud device 370. Thus, by way of example, the software 330 can be distributed across the computer system 300, to operate the display 331, the camera 334, the audio output 333, the microphone 335, and the processor 310 (e.g., which can also be connected to other part of the computer system 300), to perform any of the methods described herein.

Figure 4:
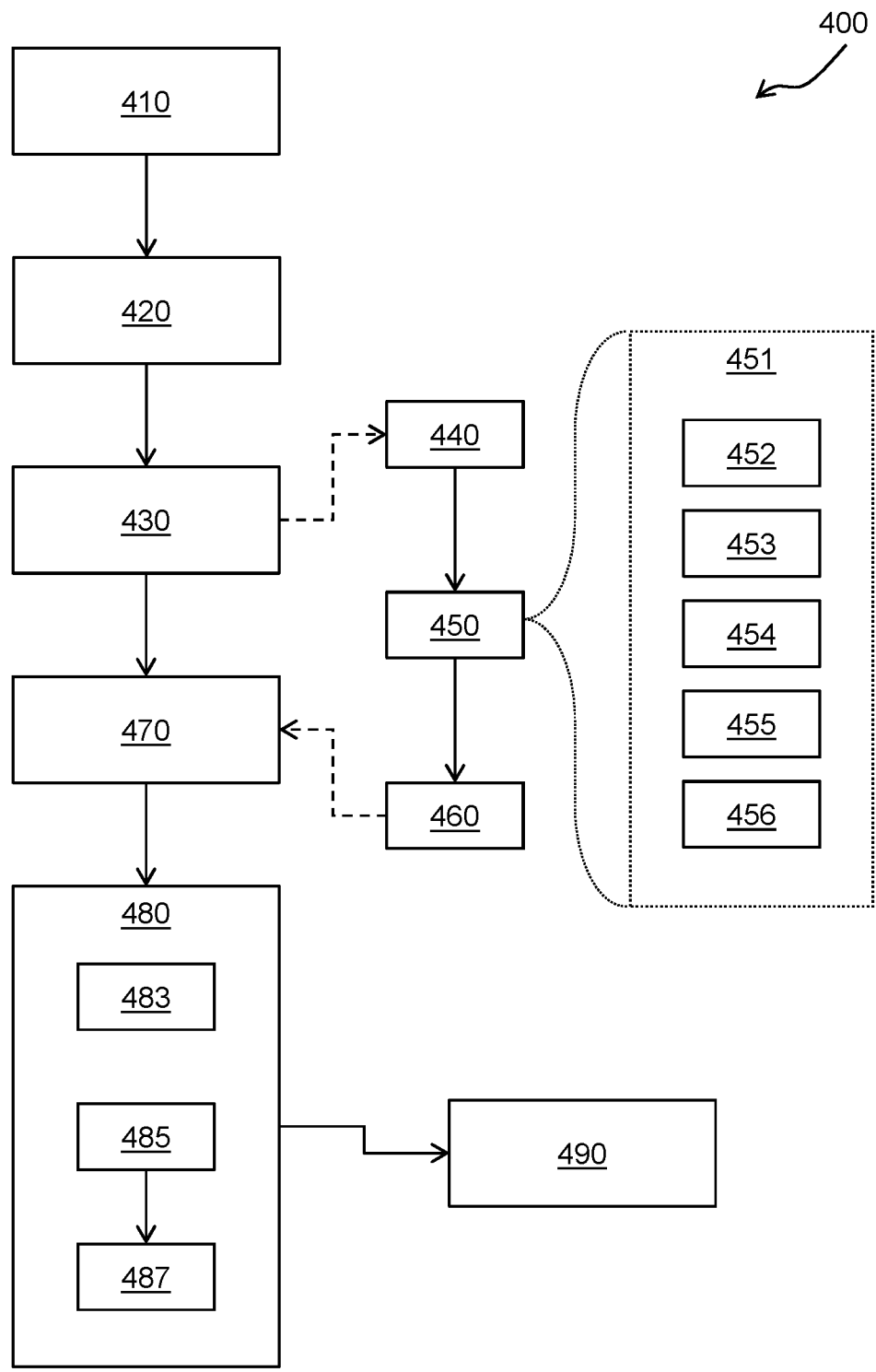
FIG. 4 depicts a method according to one or more embodiments.

Turning to FIG. 4, an exemplary method 400 of the software 330 is illustrated according to one or more embodiments. The exemplary method 400 is described with respect to FIG. 3 and provides a practical application of a speech recognition algorithm of the software 330. Generally, the speech recognition algorithm of the software 330 utilizes recordings of patient statements to produce scores. Further, the speech recognition algorithm of the software 330 can execute on the device 305 (e.g., a tablet computing device). Note that the exemplary method 400 can be stored on the system memory 320 as processor executable instructions and executed by the processor 310, as the processor 310 executes the software 330.

The exemplary method 400 begins at block 410, where the software 330 prompts the patient to say a patient statement. A patient statement can be a single word or a phrase.

At block 420, the software 330 records the patient statement. The result of recording of the patient statement can be a non-standardized patient recording. The software 330 can record the patient statement in real-time through the camera 334 and/or the microphone 335.

At block 430, the software 330 sends the non-standardized patient recording (e.g., the recording of the patient statement) to an external entity (e.g., a cloud device 370 or a second system). By way of example, the external entity can be a website, a model, or other destination within a computing environment 300.

At block 440, the external entity receives the non-standardized patient recording from the software 330. At block 450, the external entity analyzes the non-standardized patient recording. According to one or more embodiments, the external entity receives and processes the non-standardized patient recording to generate a result 451 including a neurological assessment score (e.g., process one or more relevant clipped portions of the audio to produce a neurological assessment score). The neurological assessment score can be further based on sub-scores of aspects of the non-standardized patient recording. That is, the external entity can produce and output analysis results including neurological assessment scores by processing non-standardized patient recordings and deriving sub-scores. Overall, the sub-scores represent a neurological diagnosis of the patient, and each sub-score can further represent a degree of abnormality. An average of the sub-scores can provide the neurological assessment score.

Examples of sub-scores include, but are not limited to, a quality score 452, a stress score 453, a correct syllable coefficient 454, a pronunciation 455, and a fluency 456. The correct syllable coefficient 454 can be determined by dividing a correct syllable count by an overall syllable count. The correct syllable coefficient 434 can be a percentage represented by a number from one (1) to one hundred (100).

The neurological assessment score and the sub-scores can be zero (0) or any integer selected from a range of one (1) to one hundred (100). For example, a high score can be ninety-seven (97), while a low score would be two (2).

At block 460, the external entity sends the result including the neurological assessment score to the software 330. At block 470, the software 330 receives the result including the neurological assessment score from the external entity.

At block 480, the software 330 evaluates the result. According to one or more embodiments, in evaluating the result, the software 330 can determine a minimum score from the sub-scores of the result. The minimum score can represent a relative change in speech of the patient.

By way of example, the software 330 determines the minimum score for the patient to be a zero (0). A score of zero (0) can be considered a normal score that indicates a diagnosis of no level of stroke in the patient. Thus, no action is required. A minimum score of one (1) can be considered an abnormal score that indicates diagnosis of some level of stroke in the patient.

By way of another example, the software 330 determines the minimum score for the patient to be a one (1). A score of one (1) can be considered a normal score that indicates a diagnosis of no level of stroke in the patient. Thus, no action is required. A minimum score of zero (0) can be considered an abnormal score that indicates diagnosis of some level of stroke in the patient.

At sub-block 483, the software 330 determines the minimum score to be normal. That is, the minimum score is a value that indicates a relative change in speech is less than 25%. Thus, further action is required and the method 400 can proceed to a next block 490.

At sub-block 486, the software 330 determines the minimum score to be abnormal. That is, the minimum score is a value that indicates the relative change in speech is greater than 25%. Accordingly, the speech recognition algorithm provides a fine-tuned determination (at sub-block 487) of the diagnosis on a scale.

According to one or more embodiments, the scale can be a five-level scale. A five-level scale can be, for example, one where if a relative change in speech is greater than 25%, then the score indicates a first level of stroke in the patient. Further, if the relative change in speech is greater than 40%, then the score indicates a second level of stroke in the patient. If the relative change in speech is greater than 60%, then the score indicates a third level of stroke in the patient. If the relative change in speech is greater than 80%, then the score indicates a fourth level of stroke in the patient. If the relative change in speech is greater than 90%, then the score indicates a fifth level of stroke in the patient. The software 330 is configurable to change the scale to further tuning of the speech recognition algorithm.

At block 490, the software 330 presents the result. According to one or more embodiments, in presenting the result, the software 330 can present the minimum score as a percentage in the user interface 341.

Figure 5:
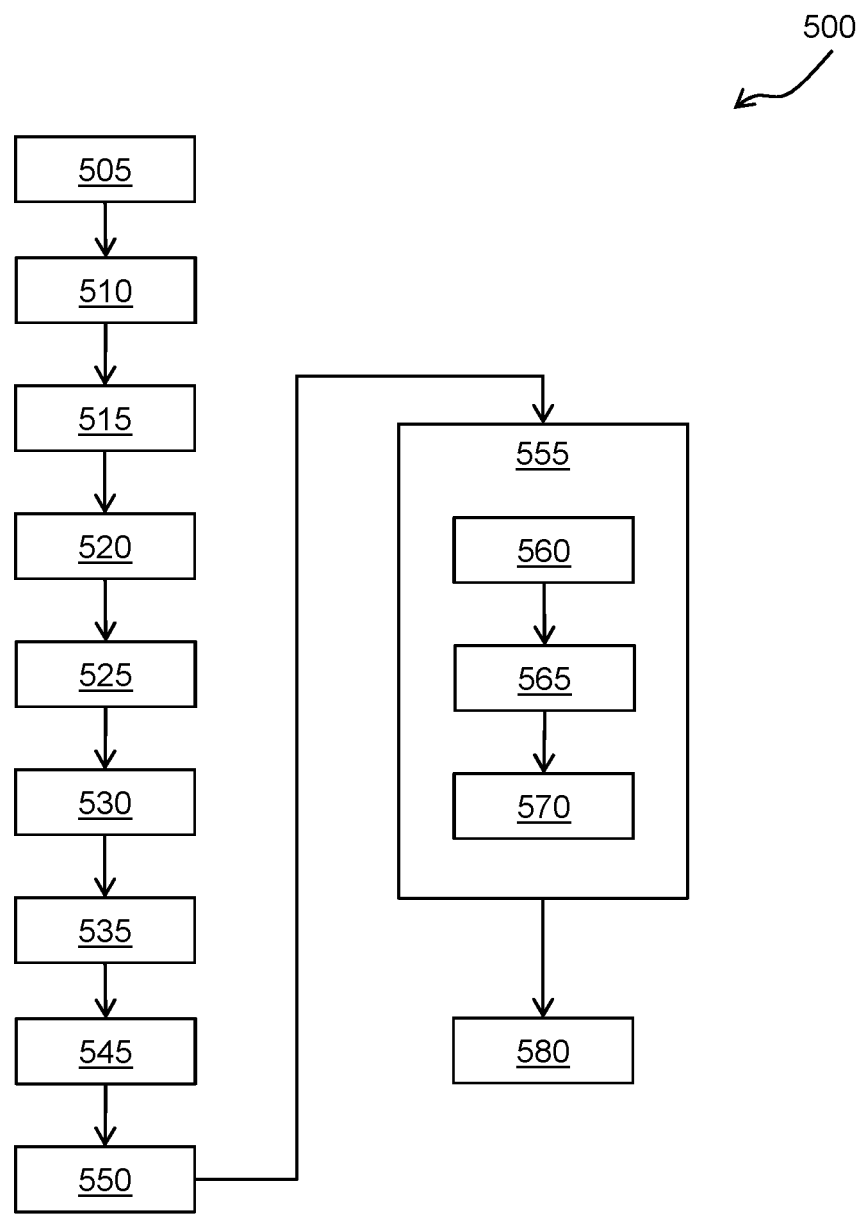
FIG. 5 depicts a method according to one or more embodiments.

Turning to FIG. 5, an exemplary method 500 of the software 330 is illustrated according to one or more embodiments. The exemplary method 500 is described with respect to FIG. 3 and provides a practical application of a hand position recognition algorithm of the software 330. Generally, the hand position algorithm of the software 330 utilizing recordings of real-time patient poses to produce scores. Further, the speech recognition algorithm of the software 330 can execute on the device 305 (e.g., a tablet computing device). Note that the exemplary method 500 can be stored on the system memory 320 as processor executable instructions and executed by the processor 310, as the processor 310 executes the software 330.

The exemplary method 500 begins at block 505, where the software 330 is set into a real-time mode with pose detection. At block 510, the software 330 starts recording a patient. The result of recording of the patient can be a non-standardized patient recording. The software 330 can record the patient in real-time (according to the real-time mode with pose detection) through the camera 334 and/or the microphone 335.

At block 515, the software 330 determines an initial state of a patient. Determining the initial state of the patient includes getting points from the recording of the patient in a staying pose. The points can include, but are not limited to, an initial left elbow, an initial left wrist, an initial left shoulder, an initial right elbow, an initial right wrist, and an initial right shoulder.

At block 520, the software 330 determines one or more distances. Determining the one or more distances includes calculating one or more of, but are not limited to, an initial left elbow distance, an initial left wrist distance, an initial right elbow distance, and an initial right wrist distance. The initial left elbow distance can be determined from subtracting the initial left shoulder from initial left elbow. The initial left wrist distance can be determined from subtracting the initial left shoulder from initial left wrist. The initial right elbow distance can be determined from subtracting the initial right shoulder from initial right elbow. The initial right wrist distance can be determined from subtracting the initial right shoulder from initial right wrist.

At block 525, the software 330 prompts the patient. The software 330 can prompt the patient to put their hands up.

At block 530, the software 330 determines a final state of a patient. Determining the final state of the patient includes getting points from the recording of the patient with their hands up. The points can include, but are not limited to, a final left elbow, a final left wrist, a final left shoulder, a final right elbow, a final right wrist, and a final right shoulder.

At block 535, the software 330 determines one or more second distances. Determining the one or more second distances includes calculating one or more of, but are not limited to, a final left elbow distance, a final left wrist distance, a final right elbow distance, and a final right wrist distance. The final left elbow distance can be determined from subtracting the final left shoulder from final left elbow. The final left wrist distance can be determined from subtracting the final left shoulder from final left wrist. The final right elbow distance can be determined from subtracting the final right shoulder from final right elbow. The final right wrist distance can be determined from subtracting the final right shoulder from final right wrist.

At block 545, the software 330 determines first relative changes. The first relative changes can be considered standardized patient information. Determining the first relative changes includes calculating differences between the first and second distances. For example, the software 330 calculates a left elbow distance change, a left wrist distance change, a right elbow distance change, and a right wrist distance change by subtracting the final points from the initial points.

At block 550, the software 330 determines second relative changes. The second relative changes can be considered standardized patient information. Determining the second relative changes includes calculating differences between the left and right distances. For example, the software 330 calculates a relative elbow change RE and a relative wrist change RW according to Equations 1 and 2.

$$RE = 100 - ABS\left(\frac{\text{MIN(LEFT ELBOW DIST CHANGE, RIGHT ELBOW DIST } CHANE\text{)}}{\text{MAX(LEFT ELBOW DIST CHANGE, RIGHT ELBOW DIST CHANGE)}}\right)\% \quad \text{Equation 1}$$

$$RW = 100 - ABS\left(\frac{\text{MIN(LEFT WRIST DIST CHANGE, RIGHT WRIST DIST } CHANE\text{)}}{\text{MAX(LEFT WRIST DIST CHANGE, RIGHT WRIST DIST CHANGE)}}\right)\% \quad \text{Equation 2}$$

At block 555, the software 330 evaluates the result. According to one or more embodiments, in evaluating the result, the software 330 identifies whether the relative elbow change RE and the relative wrist change RW are near zero percent (0%). Note that zero percent (0%) is an ideal case. If the software 330 identifies that there are differences, the method 500 proceed to score the patient for a stroke.

At sub-block 560, the software 330 determines a score. According to one or more embodiments, when the software 330 determines a relative change is less than 25%, a score for the patient is one (1). A score of one (1) is normal and indicates a diagnosis of no level of stroke in the patient. Further, when the software 330 determines the relative change is greater than 25%, score for the patient is zero (0). A score of zero (0) is abnormal and indicates diagnosis of some level of stroke in the patient.

At sub-block 565, the software 330, for scores of zero (0), the hand position recognition provides a fine-tuned determination of the diagnosis on a scale. According to one or more embodiments, the scale can be a five-level scale. A five-level scale can be, for example, one where if a relative change is greater than 25%, then the score indicates a first level of stroke in the patient. Further, if the relative change is greater than 40%, then the score indicates a second level of stroke in the patient. If the relative change is greater than 60%, then the score indicates a third level of stroke in the patient. If the relative change is greater than 80%, then the score indicates a fourth level of stroke in the patient. If the relative change is greater than 90%, then the score indicates a fifth level of stroke in the patient. The software 330 is configurable to change the scale to further tuning of the hand position recognition algorithm.

At sub-block 570, the software 330 determines a final level of stroke. The final level of stroke can be a maximum between the relative elbow change RE and a relative wrist change RW.

At block 580, the software 330 presents the result. According to one or more embodiments, in presenting the result, the software 330 can present the final level of stroke, as well as other scores and standardized patient information, in the user interface 341.

Figure 6:
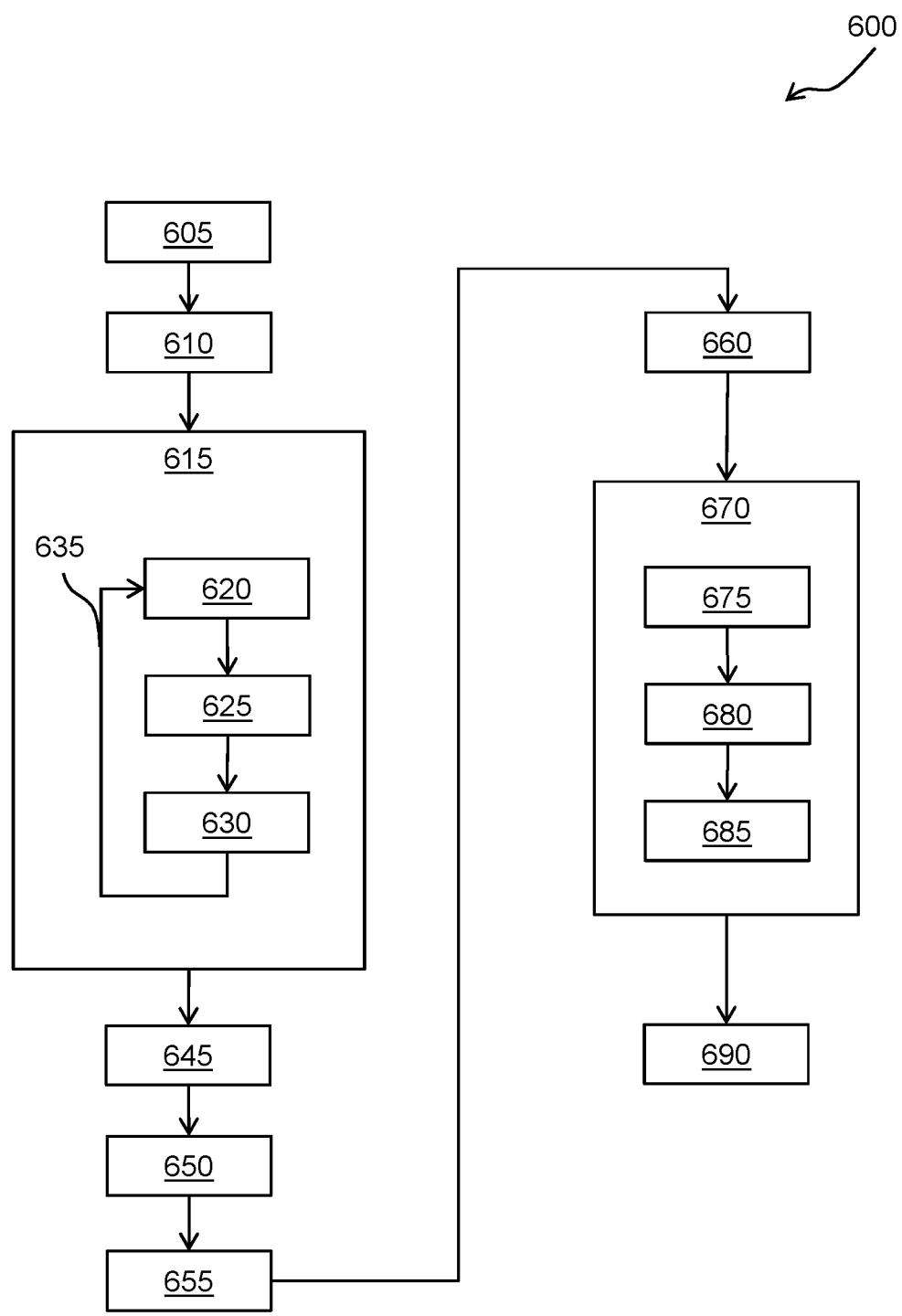
FIG. 6 depicts a method according to one or more embodiments.

Turning to FIG. 6, an exemplary method 600 of the software 330 is illustrated according to one or more embodiments. The exemplary method 600 is described with respect to FIG. 3 and provides a practical application of a face recognition algorithm of the software 330. Generally, the face algorithm of the software 330 utilizing recordings of real-time patient poses to produce scores. Further, the speech recognition algorithm of the software 330 can execute on the device 305 (e.g., a tablet computing device). Note that the exemplary method 600 can be stored on the system memory 320 as processor executable instructions and executed by the processor 310, as the processor 310 executes the software 330.

The exemplary method 600 begins at block 605, where the software 330 is set into a real-time mode with contour detection. At block 610, the software 330 starts recording a patient. The result of recording of the patient can be a non-standardized patient recording. The software 330 can record the patient in real-time (according to the real-time mode with contour detection) through the camera 334 and/or the microphone 335.

At block 615, the software 330 determines contour data sets. The contour data sets can include, but are not limited to, a left eye, a left eyebrow bottom, a left eyebrow top, a lower lip bottom, a lower lip top, a nose bottom, a right eye, a right eyebrow bottom, a right eyebrow top, a upper lip bottom. According to one or more embodiments, the contour data sets can include left eye left and/or right eye right points, which replace or supplement the corresponding left and/or right eyebrow point.

At sub-block 620, the software 330 determines an initial state of a patient. Determining the initial state of the patient includes getting contour data sets from the recording of the patient when the patient is not smiling. The initial state of contour data sets can include, but are not limited to, an initial left eye left point, an initial left brow left point, an initial left lips point, an initial right eye right point, an initial right brow right point, an initial right lips point, and an initial nose bottom point.

According to one or more embodiments, the initial state of contour data sets can include an initial left eye left point, an initial upper lip bottom let point, an initial right eye right point, and an initial upper lip bottom right point. One or more advantages, technical effects, and/or benefits include, but are not limited to, utilizing the initial left eye left point, the initial upper lip bottom let point, the initial right eye right point, and the initial upper lip bottom right point to provide a more accurate speech recognition algorithm of the software 330.

At block 625, the software 330 determines one or more distances. Determining the one or more distances includes calculating one or more of, but are not limited to, an initial left eye distance, an initial left brow distance, an initial left lips distance, an initial right eye distance, an initial right brow distance, and an initial right lips distance. The initial left eye distance can be determined from subtracting the initial nose bottom point from the initial left eye left point. The initial left brow distance can be determined from subtracting the initial nose bottom point from the initial left brow left point. The initial left lips distance can be determined from subtracting the initial nose bottom point from an initial left lips point. The initial right eye distance can be determined from subtracting the initial nose bottom point from the initial right eye right point. The initial right brow distance can be determined from subtracting the initial nose bottom point from the initial right brow right point. The initial right lips distance can be determined from subtracting the initial nose bottom point from the initial right lips point.

At sub-block 630, the software 330 prompts the patient. The software 330 can prompt the patient to smile. At arrow 635, the software 330 loops back to sub-block 620 to retrieve contour data sets while the patient is smiling. The smiling of contour data sets can include, but are not limited to, a new initial left eye left point, a new left brow left point, a new left lips point, a new right eye right point, a new right brow right point, a new right lips point, and a new nose bottom point. Note that positions of the points can change during the recording, so the software 330 obtains maximum values for the final calculation.

At block 645, the software 330 determines a final state of a patient. Determining the final state of the patient includes concluding the recording and getting contour data sets for a final list of points. The final state of contour data sets can include, but are not limited to, a final initial left eye left point, a final left brow left point, a final left lips point, a final right eye right point, a final right brow right point, a final right lips point, and a final nose bottom point.

At block 650, the software 330 determines one or more final distances. Determining the one or more second distances includes calculating one or more of, but are not limited to, a final left eye distance, a final left brow distance, a final left lips distance, and a final right eye distance, a final right brow distance, a final right lips distance. The final left eye distance can be determined from subtracting the final nose bottom point from the final left eye left point. The final left brow distance can be determined from subtracting the final nose bottom point from the final left brow left point. The final left lips distance can be determined from subtracting the final nose bottom point from the final left lips point. The final right eye distance can be determined from subtracting the final nose bottom point from the final right eye right point. The final right brow distance can be determined from subtracting the final nose bottom point from the final right brow right point. The final right lips distance can be determined from subtracting the final nose bottom point from the final right lips point.

At block 655, the software 330 determines changes. The changes can be considered standardized patient information. Determining the changes includes calculating differences between the initial and final points. For example, the software 330 calculates a left eye distance change, a left brow distance change, a left lips distance change, a right eye distance change, a right brow distance change, and a right lips distance change by subtracting the final points from the initial points.

At block 660, the software 330 determines relative changes. The relative changes can be considered standardized patient information. Determining the second relative changes includes calculating differences between the left and right sides. For example, the software 330 calculates a relative eye change RE, a relative brow change RB, and a relative lips change RL according to Equations 3, 4, and 5.

$$RE = 100 - ABS\left(\frac{MIN(LEFT\ EYE\ DIST\ CHANGE,\ RIGHT\ EYE\ DIST\ CHANE)}{MAX(LEFT\ EYE\ DIST\ CHANGE,\ RIGHT\ EYE\ DIST\ CHANGE)}\right)\%$$ Equation 3

$$RB = 100 - ABS\left(\frac{MIN(LEFT\ BROW\ DIST\ CHANGE,\ RIGHT\ BROW\ DIST\ CHANE)}{MAX(LEFT\ BROW\ DIST\ CHANGE,\ RIGHT\ BROW\ DIST\ CHANGE)}\right)\%$$ Equation 4

$$RL = 100 - ABS\left(\frac{MIN(LEFT\ LIPS\ DIST\ CHANGE,\ RIGHT\ LIPS\ DIST\ CHANE)}{MAX(LEFT\ LIPS\ DIST\ CHANGE,\ RIGHT\ LIPS\ DIST\ CHANGE)}\right)\%$$ Equation 5

At block 670, the software 330 evaluates the result. According to one or more embodiments, in evaluating the result, the software 330 identifies whether the relative eye change RE, the relative brow change RB, and the relative lips change RL are near zero percent (0%). Note that zero percent (0%) is an ideal case. If the software 330 identifies that there are differences, the method 600 proceeds to score the patient for a stroke.

At sub-block 675, the software 330 determines a score. According to one or more embodiments, when the software 330 determines a relative change is less than 25%, a score for the patient is one (1). A score of one (1) is normal and indicates a diagnosis of no level of stroke in the patient. Further, when the software 330 determines the relative change is greater than 25%, score for the patient is zero (0). A score of zero (0) is abnormal and indicates diagnosis of some level of stroke in the patient.

At sub-block 680, the software 330, for scores of zero (0), the face position recognition provides a fine-tuned determination of the diagnosis on a scale. According to one or more embodiments, the scale can be a five-level scale. A five-level scale can be, for example, one where if a relative change is greater than 25%, then the score indicates a first level of stroke in the patient. Further, if the relative change is greater than 40%, then the score indicates a second level of stroke in the patient. If the relative change is greater than 60%, then the score indicates a third level of stroke in the patient. If the relative change is greater than 80%, then the score indicates a fourth level of stroke in the patient. If the relative change is greater than 90%, then the score indicates a fifth level of stroke in the patient. The software 330 is configurable to change the scale to further tuning of the face position recognition algorithm.

At sub-block 685, the software 330 determines a final level of stroke. The final level of stroke can be a maximum between the relative eye change RE, the relative brow change RB, and a relative lips change RL.

At block 690, the software 330 presents the result. According to one or more embodiments, in presenting the result, the software 330 can present the final level of stroke, as well as other scores and standardized patient information, in the user interface 341.

Figure 7:
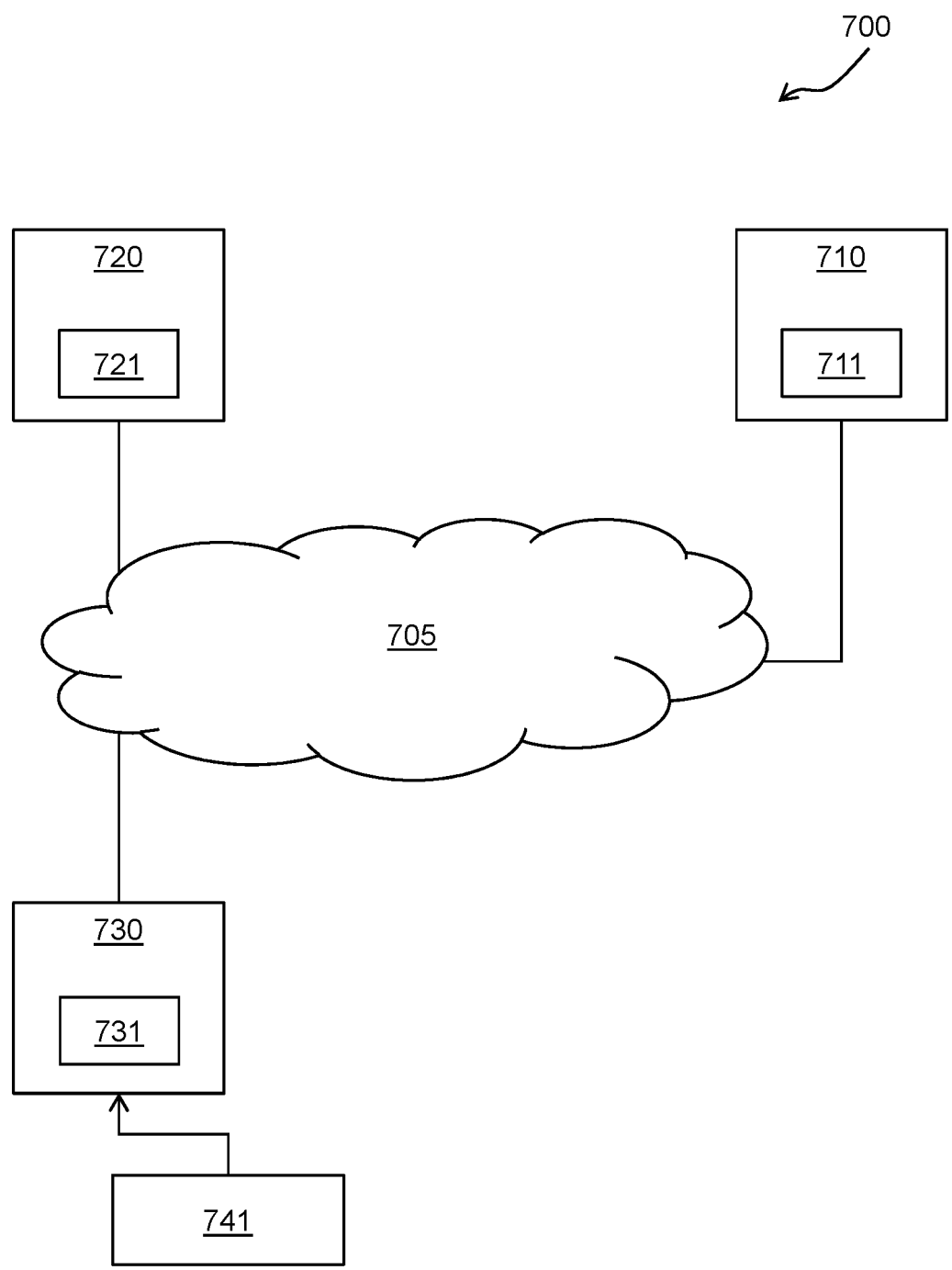
FIG. 7 depicts an environment according to one or more embodiments.

FIG. 7 depicts an environment 700 according to one or more exemplary embodiments. The environment 700 includes a network 705, a first system 710 supporting a software platform 711, a second system 720 supporting a software platform 721, and a third system 730 supporting a software platform 731, which is being engaged by a patient 741. The features and elements of the environment 700, as well as the one or more corresponding one or more operations of the environment 700, can be performed individually or in combination in any of an online environment, an offline environment, a backend processing environment, a local processing environment, a remote processing environment, a cloud processing environment, and/or other environment. Thus, the third system 730 and the software platform 731 can be provided and executed as a standalone service or integrated with a broader offering of other services by the first and second systems 710 and 720 related to medical assessments for diagnosis of neurological and other conditions.

According to one or more embodiments, the first system 710, the second system 720, and the third system 730 can be any computing system (e.g., the device 204, the first computing device 206, and/or the second computing system 208) and include any hardware and software as needed to execute the methods 100, 200, 400, 500, and 600 herein. The first system 710 is an example of a server and the software tool 711 is an example of the web-based application/tool, as described herein. The first system 710 and the software tool 711 can connect and communicate via the network 705 to the second system 720 and the third system 730, and vice-versa, as needed to execute the methods 100, 200, 400, 500, and 600 herein. The second system 720 and the third system 730 can connect and communicate to the system 710 and the software tool 711 using a web browser or application that loads one or more user interfaces, as the software platforms 721 and 731 can be implemented as client instances of the software tool 711, or independent instances. Thus, the environment 700 contemplates implementing web-server, client-server, local processing, and/or other models. The patient 741 can be representative of one or more users (whether sick themselves, and/or a care taker on behalf of a patient) interacting with the third system 730 (e.g., similarly, a clinician, a technician, or a doctor can be a user interacting with the second system 720 and the second software platform 721). Generally, the environment 700 provides the first, second, and third software platforms 711, 721, and 731 as a software/hardware workflow tool that automates one or more portions of medical assessments for diagnosis of neurological and other conditions.

According to one or more embodiments, a system for a neurological assessment is provided. The system includes a memory. The memory includes processor executable instructions for the neurological assessment. The system includes a display, an audio output, a camera, a microphone, and a processor operably coupled to the memory, the display, the audio output, the camera, and the microphone. The processor is configured to execute the processor executable instructions for the neurological assessment to cause the system to prompt a patient to perform at least one of a plurality of actions, record video and audio of the at least one of a plurality of actions as non-standardized patient specific information from the patient via the camera and the microphone, and generate one or more relevant clipped portions from the video and the audio. The one or more relevant clipped portions convert the non-standardized patient specific information into standardized patient specific information. The processor is configured to execute the processor executable instructions for the neurological assessment to cause the system to cause a determination of a neurologic status for the patient based on the standardized patient specific information by transmitting the one or more relevant clipped portions to a second system for analysis and receiving an analysis result comprising the neurologic status from the second system.

According to any of the system embodiments herein, the patient specific information can include at least one of a level of consciousness response, a best gaze response, a visual response, a facial palsy response, a motor arm response, a motor leg response, a limb ataxia response, a sensory response, a best language response, a dysarthria response, and an extinction and inattention response.

According to any of the system embodiments herein, the prompting of the patient can include providing at least one patient prompt via at least one selected from a group consisting of on the display and through the audio output.

According to any of the system embodiments herein, at least a first portion of the at least one patient prompt can be configured to be communicated to and be performed by a clinician facilitating the neurological assessment.

According to any of the system embodiments herein, the system can include a secondary display, and at least a second portion of the at least one patient prompt is displayed on the secondary display or produced through the audio output to the patient.

According to any of the system embodiments herein, the system can include a light detecting and ranging (LIDAR) device configured to obtain LIDAR data, and the processor executable instructions for the neurological assessment cause the system to generate one or more relevant clipped portions from the video, the audio, and the LIDAR data.

According to any of the system embodiments herein, the system can include a communications device, and the communications device is configured to transmit the one or more relevant clipped portions to and receive the analysis result from the second system.

According to any of the system embodiments herein, the memory including the processor executable instructions; the display; the camera; the microphone; and the processor can be contained in a machine.

According to one or more embodiments, the machine can be a tablet computing device.

According to any of the system embodiments herein, the memory including the processor executable instructions; the display; the camera; the microphone; and the processor can be distributed across one or more devices of the system.

According to one or more embodiments, a system for a neurological assessment is provided. The system includes a memory. The memory includes processor executable instructions for the neurological assessment. The system includes a display, an audio output, a camera, a microphone, and a processor operably coupled to the memory, the display, the audio output, the camera, and the microphone. The processor is configured to execute the processor executable instructions for the neurological assessment to cause the system to prompt a patient to perform at least one of a plurality of actions and record video and audio of the at least one of a plurality of actions as non-standardized patient specific information from a patient via the camera and the microphone. The processor is configured to execute the processor executable instructions for the neurological assessment to cause the system to process one or more relevant clipped portions of the video and the audio to produce a neurological assessment score for the patient. The one or more relevant clipped portions summarize the non-standardized patient specific information into a standardized patient specific information. The processor is configured to execute the processor executable instructions for the neurological assessment to cause the system to determine a neurologic status for the patient based on the neurological assessment score and implement a neurological response based on the neurologic status.

According to any of the system embodiments herein, the patient specific information can include at least one of a level of consciousness response, a best gaze response, a visual response, a facial palsy response, a motor arm response, a motor leg response, a limb ataxia response, a sensory response, a best language response, a dysarthria response, and an extinction and inattention response.

According to any of the system embodiments herein, the prompting of the patient can include providing at least one patient prompt on the display or through the audio output.

According to any of the system embodiments herein, the at least a first portion of the at least one patient prompt can be configured to be communicated to and be performed by a clinician facilitating the neurological assessment.

According to any of the system embodiments herein, the system can include a secondary display, and at least a second portion of the at least one patient prompt is displayed on the secondary display or produced through the audio output to the patient.

According to any of the system embodiments herein, the system can include a light detecting and ranging (LIDAR) device configured to obtain LIDAR data, and the processor executable instructions for the neurological assessment cause the system to record the video, the audio, or the LIDAR data of the at least one of the plurality of actions as the non-standardized patient specific information from the patient via the camera, the microphone, or the LIDAR device, respectively.

According to any of the system embodiments herein, the system can include a communications device configured to transmit the standardized patient specific information via the communications device to a second system and to receive the neurologic status from the second system.

According to any of the system embodiments herein, the memory including the processor executable instructions; the display; the camera; the audio output; the microphone; and the processor can be contained in a machine.

According to any of the system embodiments herein, the neurological response can include at least one of take no action; order physiological tests; order imaging tests; and order suspected condition tests.

According to any of the system embodiments herein, the memory including the processor executable instructions; the display; the camera; the microphone; and the processor can be distributed across one or more devices of the system.

According to one or more embodiments, a method of a neurological assessment of a patient is provided. The method is implemented by a system comprising at least a memory, a display, an audio output, a camera, a microphone, and a processor. The method includes prompting the patient to perform at least one of a plurality of actions; recording video and audio of the at least one of a plurality of actions as non-standardized patient specific information from the patient via the camera and the microphone; generating one or more relevant clipped portions from the video and the audio, the one or more relevant clipped portions converting the non-standardized patient specific information into standardized patient specific information; and causing a determination of a neurologic status for the patient based on the standardized patient specific information by transmitting the one or more relevant clipped portions to a second system for analysis and receiving an analysis result comprising the neurologic status from the second system.

According to any of the method embodiments herein, the patient specific information comprises at least one of a level of consciousness response, a best gaze response, a visual response, a facial palsy response, a motor arm response, a motor leg response, a limb ataxia response, a sensory response, a best language response, a dysarthria response, and an extinction and inattention response.

According to any of the method embodiments herein, the prompting of the patient can include providing at least one patient prompt via at least one selected from a group consisting of on the display and through the audio output.

According to any of the method embodiments herein, at least a first portion of the at least one patient prompt can be configured to be communicated to and be performed by a clinician facilitating the neurological assessment.

According to any of the method embodiments herein, the system can include a secondary display, and the method can include displaying at least a second portion of the at least one patient prompt on the secondary display or produced through the audio output to the patient.

According to any of the method embodiments herein, the system can include a light detecting and ranging (LIDAR) device configured to obtain LIDAR data, and the method can include generating the one or more relevant clipped portions from the video, the audio, and the LIDAR data.

According to any of the method embodiments herein, the system can include a communications device configured to transmit the one or more relevant clipped portions to and receive the analysis result from the second system.

According to any of the method embodiments herein, the memory including the processor executable instructions; the display; the camera; the microphone; and the processor can be contained in a machine.

According to any of the method embodiments herein, the machine can include a tablet computing device.

According to any of the method embodiments herein, the memory including the processor executable instructions; the display; the camera; the microphone; and the processor can be distributed across one or more devices of the system.

According to one or more embodiments, a method of a neurological assessment of a patient is provided. The method is implemented by a system comprising at least a memory, a display, an audio output, a camera, a microphone, and a processor. The method includes prompting a patient to perform at least one of a plurality of actions and record video and audio of the at least one of a plurality of actions as non-standardized patient specific information from a patient via the camera and the microphone; processing one or more relevant clipped portions of the video and the audio to produce a neurological assessment score for the patient, the one or more relevant clipped portions summarizing the non-standardized patient specific information into a standardized patient specific information; and determining a neurologic status for the patient based on the neurological assessment score; and implementing a neurological response based on the neurologic status.

According to any of the method embodiments herein, the patient specific information can include at least one of a level of consciousness response, a best gaze response, a visual response, a facial palsy response, a motor arm response, a motor leg response, a limb ataxia response, a sensory response, a best language response, a dysarthria response, and an extinction and inattention response.

According to any of the method embodiments herein, the prompting of the patient can include providing at least one patient prompt on the display or through the audio output.

According to any of the method embodiments herein, the at least a first portion of the at least one patient prompt can be configured to be communicated to and be performed by a clinician facilitating the neurological assessment.

According to any of the method embodiments herein, the system can include a secondary display, and the method can include displaying at least a second portion of the at least one patient prompt on the secondary display or produced through the audio output to the patient.

According to any of the method embodiments herein, the system can include a light detecting and ranging (LIDAR) device configured to obtain LIDAR data, and the method can include recording the video, the audio, or the LIDAR data of the at least one of the plurality of actions as the non-standardized patient specific information from the patient via the camera, the microphone, or the LIDAR device, respectively.

According to any of the method embodiments herein, the system can include a communications device configured to transmit the standardized patient specific information via the communications device to a second system and to receive the neurologic status from the second system.

According to any of the method embodiments herein, the memory including the processor executable instructions; the display; the camera; the audio output; the microphone; and the processor can be contained in a machine.

According to any of the method embodiments herein, the neurological response can include at least one of take no action; order physiological tests; order imaging tests; and order suspected condition tests.

According to any of the method embodiments herein, the memory including the processor executable instructions; the display; the camera; the microphone; and the processor can be distributed across one or more devices of the system.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. A computer readable medium, as used herein, is not to be construed as being transitory signals per se, for example, radio waves or other freely propagating electromagnetic waves, electromagnetic waves propagating through a waveguide or other transmission media (e.g., light pulses passing through a fiber-optic cable), or electrical signals transmitted through a wire Examples of computer-readable media include electrical signals (transmitted over wired or wireless connections) and computer-readable storage media. Examples of computer-readable storage media include, but are not limited to, a register, cache memory, semiconductor memory devices, magnetic media (e.g., internal hard disks and removable disks), magneto-optical media, optical media (e.g., compact disks (CD) and digital versatile disks (DVDs)), a random access memory (RAM), a read-only memory (ROM), an erasable programmable read-only memory (EPROM or Flash memory), a static random access memory (SRAM), and a memory stick. A processor in association with software may be used to implement a radio frequency transceiver for use in a terminal, base station, or any host computer.

The terminology used herein is for the purpose of describing particular embodiments only and is not intended to be limiting. As used herein, the singular forms "a", "an" and "the" are intended to include the plural forms as well, unless the context clearly indicates otherwise. The phrase "at least one" followed by a list of two or more items, such as "A, B, or C" or "A, B, and C" means any individual one of A, B or C as well as any combination thereof. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The descriptions of the various embodiments herein have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed:

1. A system for a neurological assessment comprising:
a memory comprising processor executable instructions for the neurological assessment;
a display;
an audio output;
a camera;
a microphone; and
a processor operably coupled to the memory, the display, the audio output, the camera, and the microphone, the processor configured to execute the processor executable instructions for the neurological assessment to cause the system to:
prompt a patient to perform at least one of a plurality of actions;
record video and audio of the at least one of a plurality of actions as non-standardized patient specific information from the patient via the camera and the microphone;
for each prompt given to the patient, generate one or more relevant clipped portions from the video and the audio, the one or more relevant clipped portions converting the non-standardized patient specific information into one or more targeted standardized patient specific information of audio or video; and
cause a determination of a neurologic status for the patient based on the standardized patient specific information by transmitting the one or more relevant clipped portions to a second system for analysis and receiving an analysis result comprising the neurologic status from the second system.

2. The system of claim 1, wherein the patient specific information comprises a level of consciousness response, a best gaze response, a visual response, a facial palsy response, a motor arm response, a motor leg response, a limb ataxia response, a sensory response, a best language response, a dysarthria response, and an extinction and inattention response.

3. The system of claim 1, wherein the prompting of the patient comprises providing at least one patient prompt via at least one selected from a group consisting of on the display and through the audio output.

4. The system of claim 3, wherein the at least one patient prompt is configured to be communicated to and be performed by a clinician facilitating the neurological assessment.

5. The system of claim 4, further comprising a secondary display, and wherein the at least one patient prompt is displayed on the secondary display or produced through the audio output to the patient.

6. The system of claim 1, wherein at least one of the one or more relevant clipped portions comprises a clip length of ten (10) to twelve (12) seconds.

7. The system of claim 1, wherein at least one of the one or more relevant clipped portions captures the at least one of the plurality of actions of the audio or video relative to the prompting as the one or more targeted standardized patient specific information.

8. The system of claim 1, wherein the processor executable instructions comprises one or more machine learning or artificial intelligence algorithms configured to clip from recordings of the video and the audio to only the one or more relevant clipped portions.

9. A system for a neurological assessment comprising:
a memory comprising processor executable instructions for the neurological assessment;
a display;
an audio output;
a camera;

a microphone; and a processor operably coupled to the memory, the display, the audio output, the camera, and the microphone, the processor configured to execute the processor executable instructions for the neurological assessment to cause the system to:

prompt a patient to perform at least one of a plurality of actions and record video and audio of the at least one of a plurality of actions as non-standardized patient specific information from a patient via the camera and the microphone;

for each prompt given to the patient, process one or more relevant clipped portions of the video and the audio to produce a neurological assessment score for the patient, the one or more relevant clipped portions summarizing the non-standardized patient specific information into one or more targeted standardized patient specific information of audio or video; and determine a neurologic status for the patient based on the neurological assessment score; and implement a neurological response based on the neurologic status.

10. The system of claim 9, wherein the patient specific information comprises a level of consciousness response, a best gaze response, a visual response, a facial palsy response, a motor arm response, a motor leg response, a limb ataxia response, a sensory response, a best language response, a dysarthria response, and an extinction and inattention response.

11. The system of claim 9, wherein the prompting of the patient comprises providing at least one patient prompt on the display or through the audio output.

12. The system of claim 11, wherein of the at least one patient prompt is configured to be communicated to and be performed by a clinician facilitating the neurological assessment.

13. The system of claim 12, further comprising a secondary display, and wherein the at least one patient prompt is displayed on the secondary display or produced through the audio output to the patient.

14. A method of a neurological assessment of a patient, the method being implemented by a system comprising at least a memory, a display, an audio output, a camera, a microphone, and a processor, the method comprising:

prompting the patient to perform at least one of a plurality of actions;

recording video and audio of the at least one of a plurality of actions as non-standardized patient specific information from the patient via the camera and the microphone;

for each prompt given to the patient, generating one or more relevant clipped portions from the video and the audio, the one or more relevant clipped portions converting the non-standardized patient specific information into one or more targeted standardized patient specific information of audio or video; and causing a determination of a neurologic status for the patient based on the standardized patient specific information by transmitting the one or more relevant clipped portions to a second system for analysis and receiving an analysis result comprising the neurologic status from the second system.

15. The method of claim 14, wherein the patient specific information comprises a level of consciousness response, a best gaze response, a visual response, a facial palsy response, a motor arm response, a motor leg response, a limb ataxia response, a sensory response, a best language response, a dysarthria response, and an extinction and inattention response.

16. The method of claim 14, wherein the prompting of the patient further comprises providing at least one patient prompt via at least one selected from a group consisting of on the display and through the audio output.

17. The method of claim 16, wherein the at least one patient prompt is configured to be communicated to and be performed by a clinician facilitating the neurological assessment.

18. The method of claim 17, wherein the system comprises a secondary display, and wherein the method further comprises displaying the at least one patient prompt on the secondary display or produced through the audio output to the patient.

19. The method of claim 14, wherein the system comprises a light detecting and ranging (LIDAR) device configured to obtain LIDAR data, and wherein the method further comprises generating the one or more relevant clipped portions from the video, the audio, and the LIDAR data.

20. The method of claim 14, wherein the system comprises a communications device configured to transmit the one or more relevant clipped portions to and receive the analysis result from the second system.

21. The method of claim 14, wherein the memory comprising processor executable instructions; the display; the camera; the microphone; and the processor are contained in a machine.

22. The method of claim 21, wherein the machine comprises a tablet computing device.

23. The method of claim 14, wherein the memory comprising processor executable instructions; the display; the camera; the microphone; and the processor are distributed across one or more devices of the system.

24. A method of a neurological assessment of a patient, the method being implemented by a system comprising at least a memory, a display, an audio output, a camera, a microphone, and a processor, the method comprising:

prompting a patient to perform at least one of a plurality of actions and record video and audio of the at least one of a plurality of actions as non-standardized patient specific information from a patient via the camera and the microphone;

for each prompt given to the patient, processing one or more relevant clipped portions of the video and the audio to produce a neurological assessment score for the patient, the one or more relevant clipped portions summarizing the non-standardized patient specific information into one or more targeted standardized patient specific information of audio or video; and determining a neurologic status for the patient based on the neurological assessment score; and implementing a neurological response based on the neurologic status.

25. The method of claim 24, wherein the patient specific information comprises a level of consciousness response, a best gaze response, a visual response, a facial palsy response, a motor arm response, a motor leg response, a limb ataxia response, a sensory response, a best language response, a dysarthria response, and an extinction and inattention response.

26. The method of claim 24, wherein the prompting of the patient comprises providing at least one patient prompt on the display or through the audio output.

27. The method of claim 26, wherein the at least one patient prompt is configured to be communicated to and be performed by a clinician facilitating the neurological assessment.

28. The method of claim 27, wherein the system comprises a secondary display, and wherein the method further comprises displaying the at least one patient prompt on the secondary display or produced through the audio output to the patient.

29. The method of claim 24, wherein the system comprises a light detecting and ranging (LIDAR) device configured to obtain LIDAR data, and wherein the method further comprises recording the video, the audio, or the LIDAR data of the at least one of the plurality of actions as the non-standardized patient specific information from the patient via the camera, the microphone, or the LIDAR device, respectively.

30. The method of claim 24, wherein the system comprises a communications device configured to transmit the standardized patient specific information via the communications device to a second system and to receive the neurologic status from the second system.

31. The method of claim 24, wherein the memory comprising processor executable instructions; the display; the camera; the audio output; the microphone; and the processor are contained in a machine.

32. The method of claim 24, wherein the neurological response comprises at least one of take no action; order physiological tests; order imaging tests; and order suspected condition tests.

33. The method of claim 24, wherein the memory comprising processor executable instructions; the display; the camera; the microphone; and the processor are distributed across one or more devices of the system.

* * * * *

UNITED STATES PATENT AND TRADEMARK OFFICE
CERTIFICATE OF CORRECTION

PATENT NO. : 12,059,265 B1
APPLICATION NO. : 18/397916
DATED : August 13, 2024
INVENTOR(S) : Matthew Hayner Klein It is certified that error appears in the above-identified patent and that said Letters Patent is hereby corrected as shown below:

In the Specification

1. In Column 11, Line 33, delete "range" and insert -- range of --, therefor.

2. In Column 16, Line 48, delete "(HnB)," and insert -- (HNB), --, therefor.

3. In Column 20, Lines 59-61, delete "$RE = 100 - ABS\left(\frac{MIN(LEFT\ ELBOW\ DIST\ CHANGE,\ RIGHT\ ELBOW\ DIST\ CHANE)}{MAX(LEFT\ ELBOW\ DIST\ CHANGE,\ RIGHT\ ELBOW\ DIST\ CHANGE)}\right)\%$"
and insert -- $RE = 100 - ABS\left(\frac{MIN(LEFT\ ELBOW\ DIST\ CHANGE,\ RIGHT\ ELBOW\ DIST\ CHANGE)}{MAX(LEFT\ ELBOW\ DIST\ CHANGE,\ RIGHT\ ELBOW\ DIST\ CHANGE)}\right)\%$ --, therefor.

4. In Column 20, Lines 63-65, delete "$RW = 100 - ABS\left(\frac{MIN(LEFT\ WRIST\ DIST\ CHANGE,\ RIGHT\ WRIST\ DIST\ CHANE)}{MAX(LEFT\ WRIST\ DIST\ CHANGE,\ RIGHT\ WRIST\ DIST\ CHANGE)}\right)\%$"
and insert -- $RW = 100 - ABS\left(\frac{MIN(LEFT\ WRIST\ DIST\ CHANGE,\ RIGHT\ WRIST\ DIST\ CHANGE)}{MAX(LEFT\ WRIST\ DIST\ CHANGE,\ RIGHT\ WRIST\ DIST\ CHANGE)}\right)\%$ --, therefor.

5. In Column 22, Line 16, delete "let point," and insert -- left point, --, therefor.

6. In Column 22, Line 20, delete "let point," and insert -- left point, --, therefor.

Signed and Sealed this
Twenty-ninth Day of October, 2024

*Katherine Kelly Vidal*
Katherine Kelly Vidal
*Director of the United States Patent and Trademark Office*

CERTIFICATE OF CORRECTION (continued)
U.S. Pat. No. 12,059,265 B1

7. In Column 23, Lines 33-35, delete "
$$RE = 100 - ABS\left(\frac{MIN(LEFT\ EYE\ DIST\ CHANGE,\ RIGHT\ EYE\ DIST\ \mathit{CHANE})}{MAX(LEFT\ EYE\ DIST\ CHANGE,\ RIGHT\ EYE\ DIST\ CHANGE)}\right)\%$$
"

and insert --
$$RE = 100 - ABS\left(\frac{MIN(LEFT\ EYE\ DIST\ CHANGE,\ RIGHT\ EYE\ DIST\ CHANGE)}{MAX(LEFT\ EYE\ DIST\ CHANGE,\ RIGHT\ EYE\ DIST\ CHANGE)}\right)\%$$
--, therefor.

8. In Column 23, Lines 37-39, delete "
$$RB = 100 - ABS\left(\frac{MIN(LEFT\ BROW\ DIST\ CHANGE,\ RIGHT\ BROW\ DIST\ \mathit{CHANE})}{MAX(LEFT\ BROW\ DIST\ CHANGE,\ RIGHT\ BROW\ DIST\ CHANGE)}\right)$$
"

and insert --
$$RB = 100 - ABS\left(\frac{MIN(LEFT\ BROW\ DIST\ CHANGE,\ RIGHT\ BROW\ DIST\ CHANGE)}{MAX(LEFT\ BROW\ DIST\ CHANGE,\ RIGHT\ BROW\ DIST\ CHANGE)}\right)\%$$
--, therefor.

9. In Column 23, Lines 41-43, delete "
$$RL = 100 - ABS\left(\frac{MIN(LEFT\ LIPS\ DIST\ CHANGE,\ RIGHT\ LIPS\ DIST\ \mathit{CHANE})}{MAX(LEFT\ LIPS\ DIST\ CHANGE,\ RIGHT\ LIPS\ DIST\ CHANGE)}\right)\%$$
"

and insert --
$$RL = 100 - ABS\left(\frac{MIN(LEFT\ LIPS\ DIST\ CHANGE,\ RIGHT\ LIPS\ DIST\ CHANGE)}{MAX(LEFT\ LIPS\ DIST\ CHANGE,\ RIGHT\ LIPS\ DIST\ CHANGE)}\right)\%$$
--, therefor.

10. In Column 29, Line 26, delete "a wire" and insert -- a wire. --, therefor.

In the Claims

11. In Column 31, Line 19, in Claim 9, delete "video; and" and insert -- video; --, therefor.

12. In Column 31, Line 34, in Claim 12, delete "wherein of" and insert -- wherein --, therefor.

13. In Column 32, Line 53, in Claim 24, delete "video; and" and insert -- video; --, therefor.